(12) United States Patent
Vacher et al.

(10) Patent No.: US 9,469,601 B2
(45) Date of Patent: Oct. 18, 2016

(54) AMINOCYCLOBUTANE DERIVATIVES, METHOD FOR PREPARING SAME AND THE USE THEREOF AS DRUGS

(71) Applicant: PIERRE FABRE MEDICAMENT, Boulogne-Billancourt (FR)

(72) Inventors: Bernard Vacher, Castres (FR); Elodie Blanc, Semalens (FR); Ronan Depoortere, Castres (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 0 days.

(21) Appl. No.: 14/649,448

(22) PCT Filed: Dec. 4, 2013

(86) PCT No.: PCT/EP2013/075481
§ 371 (c)(1),
(2) Date: Jun. 3, 2015

(87) PCT Pub. No.: WO2014/086825
PCT Pub. Date: Jun. 12, 2014

(65) Prior Publication Data
US 2015/0315132 A1 Nov. 5, 2015

(30) Foreign Application Priority Data
Dec. 4, 2012 (FR) .................................. 12 61621

(51) Int. Cl.
| | | |
|---|---|---|
| *A01N 31/16* | (2006.01) | |
| *A61K 31/165* | (2006.01) | |
| *C07C 235/40* | (2006.01) | |
| *C07C 231/14* | (2006.01) | |
| *C07C 237/24* | (2006.01) | |
| *C07D 307/00* | (2006.01) | |

(52) U.S. Cl.
CPC ........... *C07C 235/40* (2013.01); *C07C 231/14* (2013.01); *C07C 237/24* (2013.01); *C07D 307/00* (2013.01); *C07C 2101/04* (2013.01)

(58) Field of Classification Search
CPC . C07C 101/04; C07C 231/14; C07C 235/40; C07C 237/24; C07D 307/00
See application file for complete search history.

(56) References Cited

U.S. PATENT DOCUMENTS

| | | |
|---|---|---|
| 6,387,957 B1 | 5/2002 | Frome |
| 2004/0101582 A1 | 5/2004 | Wolicki |
| 2004/0204366 A1 | 10/2004 | Pasternak et al. |
| 2008/0268071 A1 | 10/2008 | Gant et al. |
| 2010/0267695 A1 | 10/2010 | Hayashibe et al. |
| 2011/0160260 A1 | 6/2011 | Ho |

FOREIGN PATENT DOCUMENTS

| | | | |
|---|---|---|---|
| EP | 0 747 348 A1 | 12/1996 | |
| EP | 0747348 A1 * | 12/1996 | ............ C07B 57/00 |
| WO | WO 98/07447 A1 | 2/1998 | |
| WO | WO 99/12537 A1 | 3/1999 | |
| WO | WO 99/52848 A1 | 10/1999 | |
| WO | WO 00/03716 A1 | 1/2000 | |
| WO | WO 00/51607 A1 | 9/2000 | |
| WO | WO 03/061656 A1 | 7/2003 | |
| WO | WO 03/063797 A2 | 8/2003 | |
| WO | WO 2006/081179 A1 | 8/2006 | |
| WO | WO 2008/092955 A1 | 8/2008 | |
| WO | WO 2009/029618 A1 | 3/2009 | |
| WO | WO 2009/069610 A1 | 6/2009 | |
| WO | WO 2009/092324 A1 | 7/2009 | |
| WO | WO 2010/036937 A1 | 4/2010 | |
| WO | WO 2010/037533 A1 | 4/2010 | |

(Continued)

OTHER PUBLICATIONS

Aarts et al., "Novel Treatment of Excitotoxicity: Targeted Disruption of Intracellular Signalling from Glutamate Receptors," Biochemical Pharmacology, vol. 66, 2003, pp. 877-886.

(Continued)

*Primary Examiner* — Jean Cornet
(74) *Attorney, Agent, or Firm* — Birch, Stewart, Kolasch & Birch, LLP

(57) ABSTRACT

The present inventions concerns derivatives of aminocyclobutane, particularly as NMDA receptor antagonists, their application in human therapy and their method of preparation.

These compounds correspond to the general formula (1):

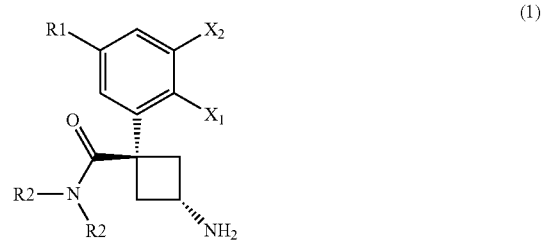

wherein:

$X_1$ represents a hydrogen atom or fluorine atom;

$X_2$ is a hydrogen atom or fluorine atom or chlorine atom;

R1 represents a hydrogen atom or fluorine atom or chlorine atom or methyl group or methoxy group or cyano group;

R2 represents independently or together a methyl group or ethyl group.

14 Claims, 1 Drawing Sheet

(56) References Cited

FOREIGN PATENT DOCUMENTS

| WO | WO 2010/112697 A1 | 10/2010 |
|----|-------------------|---------|
| WO | WO 2010/142890 A1 | 12/2010 |

OTHER PUBLICATIONS

Bardin et al., "In the Formalin Model of Tonic Nociceptive Pain, 8-OH-DPAT Produces 5-$HT_{1A}$ Receptor-Mediated, Behaviorally Specific Analgesia," European Journal of Pharmacology, vol. 421, 2001, pp. 109-114.

Beloeil et al., "The Effect of a Peripheral Block on Inflammation-Induced Prostaglandin E2 and Cyclooxygenase Expression in Rats," International Anesthesia Research Society, Anesthesia and Analgesia, vol. 109, No. 3, Sep. 2009, pp. 943-950.

Chen et al., "The Chemical Biology of Clinically Tolerated NMDA Receptor Antagonists," Journal of Neurochemistry, vol. 97, 2006, pp. 1611-1626.

Cohen et al., "Ketamine in Pain Management," Advances in Psychosomatic Medicine, vol. 30, 2011, pp. 139-161.

Depoortere et al., "Prepulse Inhibition of the Startle Reflex in Rats: Effects of Compounds Acting at Various Sites on the NMDA Receptor Complex," Behavioural Pharmacology, vol. 10, No. 1, 1999, pp. 51-62.

Elia et al., "Ketamine and Postoperative Pain—A Quantitative Systematic Review of Randomised Trials," Pain, vol. 113, 2005, pp. 61-70.

Finch et al., "Reduction of Allodynia in Patients with Complex Regional Pain Syndrome: a Double-Blind Placebo-Controlled Trial of Topical Ketamine," Pain, vol. 146, 2009, pp. 18-25.

French Preliminary Search Report, dated Aug. 2, 2013, for French Application No. 1261621.

Heusler et al., "Differential Ion Current Activation by Human 5-$HT_{1A}$ Receptors in Xenopus Oocytes: Evidence for Agonist-Directed Trafficking of Receptor Signalling," Neuropharmacology, vol. 49, 2005, pp. 963-976.

International Search Report and Written Opinion of the International Searching Authority (Forms PCT/ISA/220 and PCT/ISA/210), dated Feb. 21, 2014, for International Application No. PCT/EP2013/075481.

Johannes et al., "The Prevalence of Chronic Pain in United States Adults: Results of an Internet-Based Survey," The Journal of Pain, vol. 11, No. 11, Nov. 2010, pp. 1230-1239.

Karadottir et al., "NMDA Receptors Are Expressed in Oligodendrocytes and Activated in Ischaemia," Nature, vol. 438, Dec. 2005, pp. 1162-1166.

Mony et al., "Allosteric Modulators of NR2B-Containing NMDA Receptors: Molecular Mechanisms and Therapeutic Potential," British Journal of Pharmacology, vol. 157, 2009 (published online Jul. 8, 2009), pp. 1301-1317.

Muir, "Glutamate-Based Therapeutic Approaches: Clinical Trials with Nmda Antagonists," Current Opinion in Pharmacology, vol. 6, 2006 (available online Dec. 15, 2005), pp. 53-60.

Piepoli et al., "Glutamate Signaling in Chondrocytes and the Potential Involvement of NMDA Receptors in Cell Proliferation and Inflammatory Gene Expression," Osteoarthritis and Cartilage, vol. 17, No. 8, 2009, pp. 1076-1083.

Planells-Cases et al., "A Novel N-Methyl-D-aspartate Receptor Open Channel Blocker with in Vivo Neuroprotectant Activity," Journal of Pharmacology and Experimental Therapeutics, vol. 302, No. 1, 2002, pp. 163-173.

Salter et al., "NMDA Receptor Expression and Roles in Human Articular Chondrocyte Mechanotransduction," Biorheology, vol. 41, 2004, pp. 273-281.

Soltani Rad et al., "A Simple One-Pot Procedure for the Direct Conversion of Alcohols Into Azides Using TSLM," Tetrahedron Letters, vol. 48, 2007 (available online Mar. 12, 2007), pp. 3445-3449.

Wallace et al., "A Randomized, Double-Blind, Placebo-Controlled Trial of a Glycine Antagonist in Neuropathic Pain," Neurology, vol. 59, Dec. 2002, pp. 1694-1700.

Wilder-Smith et al., "Preoperative Back Pain is Associated With Diverse Manifestations of Central Neuroplasticity," Pain, vol. 97, 2002, pp. 189-194.

Williams et al., "A New General Method for Preparation of N-Methoxy-N-Methylamides. Application in Direct Conversion of an Ester to a Ketone," Tetrahedron Letters, vol. 36, No. 31, 1995, pp. 5461-5464.

Zarantonello et al., "Novel Analogues of Ketamine and Phencyclidine as NMDA Receptor Antagonists," Bioorganic & Medicinal Chemistry Letters, vol. 21, 2011 (Available online Feb. 18, 2011), pp. 2059-2063.

Zarate et al., "A Randomized Trial of an N-methyl-D-aspartate Antagonist in Treatment-Resistant Major Depression," Arch Gen Psychiatry, vol. 63, Aug. 2006, pp. 856-864.

International Search Report issued in PCT/EP2013/075481, mailed on Feb. 21, 2014.

* cited by examiner

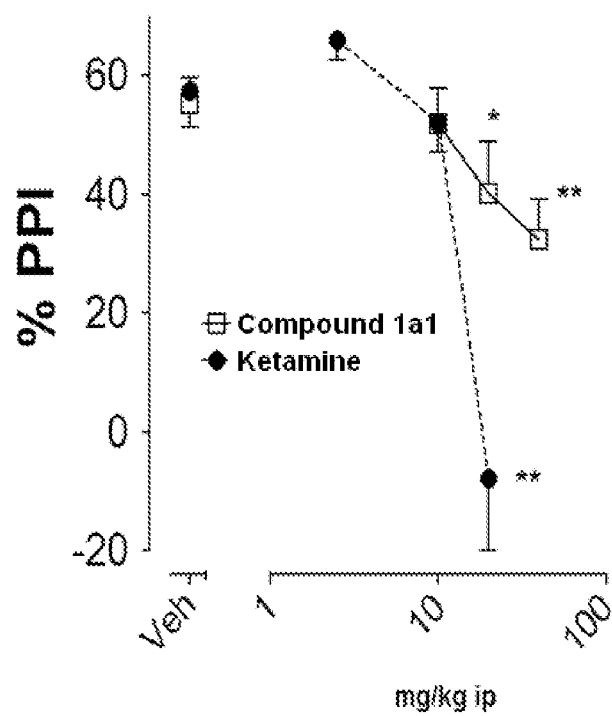

AMINOCYCLOBUTANE DERIVATIVES, METHOD FOR PREPARING SAME AND THE USE THEREOF AS DRUGS

The present invention concerns derivatives of aminocyclobutane as well as their method of preparation and their use in human therapy.

Glutamate receptors of the NMDA subtype (N-methyl-D-aspartic acid) are ionotropic receptors, mainly permeable to $Ca^{++}$ ions. Physiologically, their activation triggers the opening of an ion channel and the production of an incoming current which is only slowly inactivated. Stimulation of this receptor requires the simultaneous presence of glutamate (endogenous agonist) and glycine or D-serine (endogenous co-agonists) as well as depolarisation of the plasma membrane initiated by non-NMDA currents. The NMDA receptors are widely spread throughout the central nervous system and are also present at the periphery. They are found in the neurones, astrocytes and oligodendrocytes (Karadottir et al., 2005, *Nature*, 438, 1162-1166). At the neuronal level, they are located mainly in the post-synapse but also in extra-synaptic regions along the axons. The NMDA receptors play a key role in communication and in neuronal plasticity as well as in excitotoxicity.

The physiological activity of the NMDA receptors is essential for normal neuronal function (Chen and Lipton, 2006, *J. Neurochem.*, 97, 1611-1626). On the other hand, over activation of these receptors is involved both in acute neuronal disorders, for example strokes or cranial traumas, and in chronic stress conditions, for example neurodegenerative disorders. It is also one of the main causes of hyperexcitation leading to epilepsy seizures. There are numerous pathologies considered to be associated with NMDA receptor hyperactivity and therefore potentially sensitive to NMDA antagonists. The following can be given as examples: epilepsy, neurodegenerative disorders such as Huntington's disease, Parkinson's disease, Alzheimer's disease, strokes, amylotrophic lateral sclerosis or multiple sclerosis, AIDS-related dementia, anxiety, depression and pain syndromes.

In the present invention, the Applicant focuses in particular on the anti-depressant and analgesic properties of NMDA receptor antagonists of formula (1).

In the context of the present invention, the term "chronic pain" designates painful syndromes which progress over a period of more than three months but whose severity can vary over the course of time. On the other hand, the term "acute pain" designates pain which lasts less than three months.

Within the scope of the present invention, pain is defined as an abnormal, unpleasant, even distressing, sensory and emotional experience which is perceived and integrated at the highest level of the cerebral cortex, which gives it an emotional and affective nature. By "analgesia", we refer to a decrease in the intensity of the pain felt in response to a painful stimulus. By "analgesic medication" (or "analgesics"), we refer to a medication which relieves or suppresses the pain without leading to a loss of sensation or consciousness.

Pain of differing aetiologies requires different therapeutic strategies. In general, there are several categories of pain depending on the mechanisms involved:

pain due to excessive nociception resulting from lesions or excitation (for example inflammation) of the peripheral or visceral tissues;

neuropathic (or neurogenic) pain is related to a lesion or to dysfunctioning or disruption of the somatosensory system; it differs from nociceptive pain in that it has a different semiology;

psychogenic (or idiopathic pain) is pain which exists in the absence of lesions. The physiological mechanisms of this type of pain are not clearly defined. It is generally resistant to analgesics.

Nevertheless, certain pains have characteristics that are common to several types of pain. For example, this is the case for lower back or cancer pain which present in the form of pain caused by excessive nociception, or in the form of neuropathic pain or, in most cases, a mixture of the two.

Depression is defined in psychiatry as a mood disorder. It is characterised by a loss of motivation associated or not with different symptoms such as hopelessness, low self-esteem, anxiety, anguish and, in extreme cases, hallucinations. It is often multi-factorial and generally has multiple causes.

It is reported that approximately 7% of Europeans suffer from depression and that a third of these are resistant to clinically used antidepressants. The cost of depression in the 15-44 year old age group for society is among the highest of all known pathologies. One objective of the present invention is to describe new NMDA antagonists which have advantageous properties in this indication for which existing treatments are not entirely satisfactory.

It has been shown in mice that chronic administration of antidepressants which have different mechanisms of action (monoamine oxidase inhibitors, tricyclics, serotonin reuptake inhibitors (SSRI), or mixed serotonin and noradrenalin reuptake inhibitors) modifies the distribution and density of the NMDA receptors. In rats, acute administration by intraperitoneal route of ketamine, an NMDA receptor antagonist, reduces the immobility time in the forced swimming test, a recognised pre-clinical model for detecting the antidepressant activity of molecules. In addition, recent studies indicate that ketamine has antidepressant properties in humans. Thus administration of a single sub-anaesthetic dose of ketamine by intravenous route to patients with resistant depression significantly improves their condition and this just 2 hours after injection. The antidepressant effects obtained moreover last over a week (Zarate et al., 2006, *Arch. Gen. Psychiatry*, 63, 856-864). The rapidity of this action contrasts with the time taken for a reaction to occur with conventional antidepressants, in other words first-generation tricyclics, and the SSRIs or SNRIs which require several weeks of treatment before any beneficial effect is obtained. It therefore seems that NMDA receptor antagonists, and in particular ketamine, are effective in the treatment of depression, especially in the treatment of depression resistant to existing medications.

The therapeutic requirements of pain treatment are considerable. In fact, an incalculable number of individuals suffer from acute pain and over one in five adults both in Europe and the United States suffer from chronic pain (Johannes et al., 2010, *J. Pain*, 11, 1230-1239). The object of the present invention is to describe the advantageous analgesic properties that the compounds of formula (1) possess as well as the therapeutic perspectives they open up in the treatment of acute and chronic pain.

Many studies on animals and humans have shown that NMDA receptor antagonists such as ketamine can alleviate many aetiological types of pain such as, for example, neuropathic, postoperative or cancer pain (Cohen et al., 2011, *Adv. Psychosom. Med.*, 30, 139-161). Thus ketamine by intravenous route reduces neuropathic pain in patients resistant to treatment by conventional antidepressants. It also improves allodynia and hyperalgia in patients with CRPS (complex regional pain syndrome) (Finch et al., 2009, *Pain,* 146, 18-25). As an adjuvant, perioperative administration of a low dose of ketamine reduces the consumption of analgesics and limits acute morphine tolerance following surgery (Elia et Tramer, 2005, *Pain,* 113, 61-70). As preventive treatment, ketamine and dextromethorpan (another NMDA antagonist) improve the management of postoperative pain (Muir, 2006, *Current Opinion in Pharmacology,* 6, 53-60). Ketamine also seems to prevent the occurrence of chronic postoperative pain. (Wilder-Smith et al., 2002, *Pain,* 97, 189-194). The results obtained with other NMDA antagonists such as amantadine or MK-81 in neuropathic pain are nonetheless non-conclusive (Muir, 2006, already cited).

Opening of the NMDA channels causes an increase in intracellular calcium which activates, among others, NO synthetase and type II cyclooxygenase, leading to prostaglandin synthesis (PGs). By inhibiting the PGs, especially PGE2, NMDA antagonists thus have a direct impact on the regulation of inflammatory conditions (Beloeil et al., 2009, *Anesth. Analg.,* 109, 943-950). This complementary anti-inflammatory activity of the NMDA antagonists can be advantageous in the treatment of acute or chronic pain of inflammatory origin. Similarly, NMDA receptors are expressed in the chondrocytes and contribute to the mechanical function of cells (Salter et al., 2004, *Biorheology,* 41, 273-281). In particular, they appear to be involved in their proliferation and in inflammation leading to the destruction of joint cartilage (Piepoli et al., 2009, *Osteoarthritis and Cartilage,* 17, 1076-1083). As the latter is not regenerated in adults, use of an NMDA antagonist therefore seems to be particularly advantageous in preventing or slowing down the destruction of joint cartilage that accompanies certain pathological conditions, such as, for example, inflammatory monoarthritis, rheumatoid arthritis, septic arthritis, osteoarthritis, rheumatoid arthritis, gout, spondylarthritis, acute abarticular rheumatism.

Nevertheless, the clinical usefulness of NMDA antagonists in humans is limited by their unwanted effects, in particular on the central nervous system, and especially in the course of repeated treatment. Among the side effects of NMDA antagonists, we can cite for example: hallucinations, confusion, personality disorders, nightmares, agitation, lack of concentration, mood changes, convulsions, sedation, somnolence, nausea (Aarts et Tymianski, 2003, *Biochem. Pharmacol.,* 66, 877-886). These side effects result from the fact that NMDA antagonists block not only the excessive activation of the glutamate/NMDA system but also disrupt its normal physiological function. It therefore appears to be essential in practice to improve the risk-benefit ratio of clinically available NMDA antagonists.

When the type of pain to be treated is suitable, for example in the case of arthritis, the risk-benefit ratio of the NMDA antagonist can be improved by limiting its action on the central nervous system, for example by means of topical application. The concentration of the compound in the target tissue is therefore very much higher than its concentration in the blood, thus reducing the risk of toxicity. Consequently, several NMDA antagonists have been studied by epidural or topical route. Ketamine applied locally has been shown to be effective in the treatment of neuropathic pain not alleviated by conventional medications. Different associations of an NMDA antagonist and one or more other analgesic agents have also been studied in local application. For example, ketamine or other NMDA antagonists have been combined with antidepressants or antihypertensives (U.S. Pat. No. 6,387,957); anti-epileptics (WO 03/061656, WO 98/07447, WO 99/12537, US 20040204366, WO 2010036937); adrenergic agonists (US 20040101582); or opioids (WO 2000003716).

Given the vital role played by NMDA receptors in a number of psychiatric and neurological disorders, they have been the subject of intensive research and a multitude of antagonists/blockers/modulators have been described. They can be broadly classified in three main groups as a function of their site of action on the NMDA receptor. They therefore include:

1. Competitive antagonists targeting either the glutamate binding site, for example selfotel, perzinfotel and the pro-drugs (WO 2009029618) or the glycine binding sites for example gavestinel, GV-196771 (Wallace et al., 2002, *Neurology,* 59, 1694-1700) and the quinolines reported in patent application WO 2010037533. This category also includes partial agonists of the glycine sites such as D-cycloserine (US 2011160260).

2) Non-competitive (or allosteric) antagonists which act on many modulator sites of receptor regulation, such as, for example, the polyamine and phenylethanolamine sites. Compounds belonging to this family are currently the most clinically studied. One of the top contenders is ifenprodil (23210-56-2) and more selective derivatives of the latter for the NMDA receptor are currently undergoing clinical evaluation such as, for example, traxodopril, RGH-896, MK-0657, EVT-101 and EVT-103 (Mony et al., 2009, *Br. J. Pharmacol.,* 157, 1301-1317).

3) Non-competitive antagonists, channel pore blockers. This is the family which has had the most success clinically because ketamine (Ketalar®, anaesthetic/analgesic), dextromethorphan (Atuxane®, antitussive), memantine (Ebixa®, anti-Alzheimer), amantadine (Mantadix®, antiviral then antiparkinsonian), felbamate (Taloxa®, anticonvulsant) are commercially available. Phencyclidine (Sernyl®) developed as an anaesthetic has been withdrawn from the market and dizocilpine (MK-801) is not commercially available as a medication.

The compounds of the invention belong to this latter family of non-competitive antagonists which block the NMDA receptor channels. A major advantage of compounds of this type resides in the fact that they do not block the channel except when it is open; they are therefore more effective the more excessive the NMDA receptor activity. We can also easily see that the biophysical characteristics of the blocker/antagonist, which affects the frequency and duration of channel opening, will play a critical role in its pharmacological activity and its risk/benefit ratio. Several compounds of this type have been clinically studied such as, for example, CNS-5161 (160754-76-7), neramexane (219810-59-0), dimiracetam (126100-97-8), V-3381 (1104525-45-2), NEU-2000 (640290-67-1). Others are at the pre-clinical stage, among which we cite as examples the oxazolidines claimed in patent application WO 2009092324, indanes (WO 2009069610), diarylethylamines (WO 2010074647), arylcyclohexylamines (WO 2010142890), ketamine and phencyclidine analogues (Zarantonello et al., 2011, *Bioorg. Med. Chem. Lett.,* 21, 2059-2063).

The present invention concerns the derivatives represented by general formula (1):

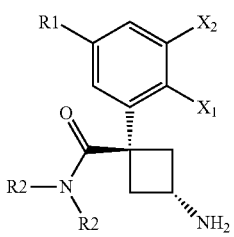

(1)

wherein:
$X_1$ represents a hydrogen atom or fluorine atom;
$X_2$ is a hydrogen atom or fluorine atom or chlorine atom;
R1 represents a hydrogen atom or fluorine atom or chlorine atom or methyl group or methoxy group or cyano group;
R2 represents independently or together a methyl group or ethyl group.

Preferably, the compounds of general formula (1) according to the invention are those in which:
$X_1$ represents a hydrogen atom or fluorine atom;
$X_2$ is a hydrogen atom or fluorine atom or chlorine atom;
R1 a hydrogen atom or fluorine atom or chlorine atom or methyl group or methoxy group or cyano group;
R2 is an ethyl group.

The compounds of the invention may intervene as pure diastereoisomers or as mixtures of diastereoisomers. More specifically, the invention relates to pure diastereoisomers in which the 1-carboxamide group and the 3-amino group occupy opposite sides of the plane defined by cyclobutane. This stereochemical relationship between said substituents is termed 'trans' in the present invention. The invention therefore relates to pure trans diastereoisomers of the following products:
trans-3-amino-N,N-diethyl-1-phenylcyclobutanecarboxamide,
trans-3-amino-N,N-dimethyl-1-phenylcyclobutanecarboxamide
trans-3-amino-N,N-diethyl-1-(2-fluorophenyl)-cyclobutanecarboxamide,
trans-3-amino-N,N-diethyl-1-(3-methoxyphenyl)-cyclobutanecarboxamide,
trans-3-amino-N,N-diethyl-1-(3-fluorophenyl)-cyclobutanecarboxamide,
trans-3-amino-N,N-diethyl-1-(3-chlorophenyl)-cyclobutanecarboxamide,
trans-3-amino-N,N-diethyl-1-(3-methylphenyl)-cyclobutanecarboxamide,
trans-3-amino-N,N-diethyl-1-(3-cyanophenyl)-cyclobutanecarboxamide,
trans-3-amino-N,N-diethyl-1-(2-fluoro-3-chlorophenyl)-cyclobutanecarboxamide,
trans-3-amino-N,N-diethyl-1-(2,5-difluorophenyl)-cyclobutanecarboxamide,
trans-3-amino-N,N-diethyl-1-(3,5-difluorophenyl)-cyclobutanecarboxamide,
trans-3-amino-N,N-diethyl-1-(3,5-dichlorophenyl)-cyclobutanecarboxamide.
as well as their pharmaceutically acceptable salts.

The term "pure diastereoisomers" designates that the 'trans' diastereoisomer of the compound of general formula (1) contains less than 5% of the 'cis' diastereoisomer, in other words the one in which the 1-carboxamide group and the 3-amino group occupy the same half-space of the plane defined by cyclobutane.

The term "diastereoisomers" designates in the context of the present invention stereoisomers which are not mirror images of each other.

The term "steroisomers" designates in the context of the present invention isomers of identical constitution but which differ in terms of the arrangement of their atoms in space.

The closest state of the technique is represented by the derivatives described in patent application WO 2003063797 and having the following formula:

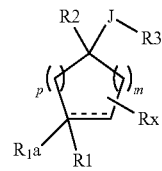

wherein:
m and p are independently equal to 0, 1, 2 or 3;
The dotted line represents a double bond when $R_1a$ is absent;
R1 can be a $NR_6R_7$ group with $R_6$ and $R_7$ possibly representing a hydrogen atom;
$R_1a$ can be a hydrogen atom;
R2 can be an aryl group substituted or unsubstituted;
J can be a bond;
R3 can be a —$C(Z_1)$—$R_5$ group with $R_5$ possibly representing a $NR_6aR_7a$ group;
$R_6a$ and $R_7a$ possibly represent an alkyl group substituted or unsubstituted and $Z_1$ possibly represents a carbonyl group (C=O);
Rx can be one or several substituted or non-attached group(s) to all the available carbon atoms in the ring but also a hydrogen atom.

This patent application therefore covers a considerable number of compounds, the large majority of which are of the cyclobutane type (m=O and p=1). Among the latter only four are given as examples in said patent. This concerns the compounds of the following formula:

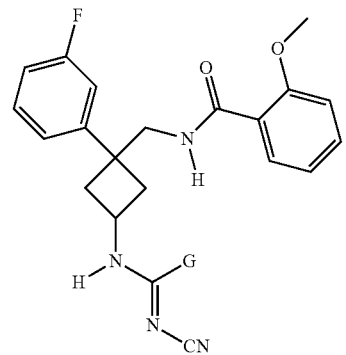

wherein G is a $NH_2$ or $N(CH_3)_2$ or $NH(CH_2CH_3)$ or $NH(CH_2CHCH_2)$ group.

The compounds in this patent application are claimed as inhibitors of the current produced by type Kv1 voltage-dependent potassium channels and in particular the current produced by isoform Kv1.5.

They are presented as useful in a broad range of indications that does not include the treatment of depression or pain.

It is important to mention that the compounds of the present invention do not interact with the potassium channels and in particular with type Kv1.5 channels. Moreover, the NMDA antagonist activity of the compounds of the invention is found to be highly sensitive to structural changes in the compounds of formula (1). Thus the NMDA antagonist activity is suppressed when:

1) The 1-carboxamide group is reduced to a 1-aminomethyl group, such as that of the cyclobutane compounds of patent WO 2003/063797;

2) The amino group in position 3 on cyclobutane is different from a primary amine group (NH$_2$). In patent application WO 2003063797, the 3-amino group is substituted by a C(G)=NCN group;

3) The "cis" stereochemistry between the 1-aryl and 3-amino groups is not present. In fact when the 1-aryl and 3-amino groups are in "trans" stereochemistry, the corresponding compounds have no affinity for the NMDA receptor.

The state of the technique is also represented by the derivatives described in patent application WO 99/52848 and corresponding to the following formula:

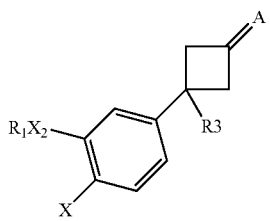

wherein:

X is different from a hydrogen atom;

A can be an NR$_7$ group with R$_7$ different from a hydrogen atom;

R3 can be a C(O)NR$_8$R$_{10}$ group in which R$_8$ and R$_{10}$ can be C$_1$-C$_4$ alkyl chains. Said compounds are claimed as being selective inhibitors of type 4 phosphodiesterases, useful for treating inflammatory and autoimmune diseases. The compounds of the present invention therefore differ from those described in application WO 99/52848 in terms of both their chemical structure and their pharmacological activity.

The state of the technique is also represented by the derivatives described in patent application WO 2010/112597 and having the general formula:

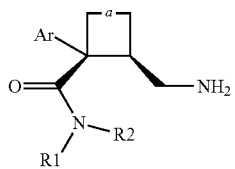

wherein:

a can be a single bond;

Ar represents a phenyl group substituted or unsubstituted, or a pyridine-3-yl core substituted by one or more halogen atom or alkyl groups or alkoxide groups or by a cyano group;

R1 and R2 can represent independently or together a C$_1$-C$_6$ alkyl group.

Contrary to the compounds of patent application WO 2010/112597, those of the present invention do not have affinity for the serotonin and noradrenalin reuptake sites. The compounds of formula (1) therefore differ from those described in application WO 2010/112597 not only in terms of their chemical structure but also in terms of their pharmacological activity.

The state of the technique is finally represented by the compounds described in patent application WO 2000/051607 and having the general formula:

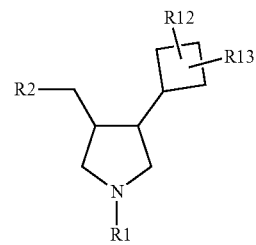

wherein R12 and R13 represent a C$_1$-C$_6$ alkyl group or a C$_2$-C$_6$ alkenyl group or a C$_2$-C$_6$ alkynyl group substituted or unsubstituted.

Said derivatives are chemokine modulators useful in the prevention or treatment of certain inflammatory or immune system diseases. Here again the compounds of the present invention thus differ from those described in application WO 2000/051607, in terms of both their chemical structure and their pharmacological activity.

The present invention also covers salts of the derivatives of general formula (1) with pharmaceutically acceptable organic or mineral acids. In the present invention, the term "pharmaceutically acceptable" refers to molecular entities and compositions which have no adverse or allergic effect or any unwanted reaction when administered to humans. When used here, the term "pharmaceutically acceptable excipient" includes any diluents, adjuvants or excipients, such as preservatives, fillers, disintegrating agents, wetting agents, emulsifiers, dispersing agents, antibacterial or antifungal agents, or even agents which help delay intestinal and digestive absorption and resorption. The use of these media or carriers is well known to the person skilled in the art. The term "pharmaceutically acceptable salts" of a compound refers to the salts defined here and which possess the pharmacological activity of the parent compound. Such salts include: acid addition salts formed with mineral acids, such as hydrochloric acid, hydrobromic acid, sulphuric acid, nitric acid, phosphoric acid and similar, or formed with organic salts, such as acetic acid, benzensulphonic acid, benzoic acid, camphorsulphonic acid, citric acid, ethanesulphonic acid, fumaric acid, glucoheptonic acid, gluconic acid, glutamic acid, glycolic acid, hydroxynaphtoic acid, 2-hydroxyethanesulphonic acid, lactic acid, maleic acid, malic acid, mandelic acid, methanesulphonic acid, muconic acid, 2-napthalenesulphonic acid, proprionic acid, salicylic acid, succinic acid, dibenzoyl-L-tartic acid, tartric acid, p-toluenesulphonic acid, trimethylacetic acid, trifluoroacetic acid and similar.

The pharmaceutically acceptable salts also include solvent (solvates) addition forms or crystalline forms (polymorphs), such as defined here, of the same acid addition salt.

The present invention also covers compounds of formula (1) as well as their pharmaceutically acceptable salts for use as medication.

The present invention concerns compounds of formula (1) as well as their pharmaceutically acceptable salts for use as NMDA receptor antagonists.

The present invention also concerns compounds of formula (1) as well as their pharmaceutically acceptable salts for use as medication intended for the treatment and/or prevention of depression.

The present invention also concerns compounds of formula (1) as well as their pharmaceutically acceptable salts for use as medication for the treatment of pain, especially pain due to excessive nociception, neuropathic pain and mixed pain.

Among the types of pain potentially sensitive to the action of compounds of general formula (1), we can cite more particularly as non-limiting examples:

Peripheral or central neuropathic pain resulting from nerve lesions of traumatic origin (for example stroke), metabolic origin (for example diabetes), infectious origin (for example HIV, shingles, herpes), trigeminal neuralgia, pain due to chemotherapy and/or radiotherapy;

inflammatory pain, for example rheumatoid arthritis, septic arthritis, osteoarthritis, polyarthritis, gout, spondylarthritis, acute abarticular rheumatism, visceral pain, for example irritable bowel syndrome, Crohn's disease;

Pain due to excessive nociception, such as posttraumatic pain, postoperative pain, burns, twisting/distension, renal or hepatic colic attacks, joint pain, arthritis, spondylarthropathies;

Mixed pain such as cancer pain, back and lower back pain or other types of pain that are difficult to classify such as headaches, fibromyalgia, pain associated with vascular/ischemic problems such as angina, Reynaud's disease.

The present invention also concerns compounds of formula (1) as well as their pharmaceutically acceptable salts for use as medication for the treatment and/or prevention of inflammation of the joints. Among the types of inflammation potentially sensitive to the action of the compounds of general formula (1), we can more particularly cite as a non-limiting examples: inflammatory monoarthritis, rheumatoid arthritis, septic arthritis, osteoarthritis rheumatoid polyarthritis, gout, spondylarthritis, acute abarticular rheumatism.

The present invention moreover concerns a pharmaceutical composition characterised in that it contains at least one compound of general formula (1) or one of its pharmaceutically acceptable salts as the active principle.

The invention also covers a pharmaceutical composition characterised in that it includes at least one compound of general formula (1) or one of its pharmaceutically acceptable salts and at least one pharmaceutically acceptable excipient.

The invention also covers a pharmaceutical composition for use as a medication for the treatment and/or prevention of depression.

The invention further covers a pharmaceutical composition for use as a medication for the treatment of pain, particularly pain caused by excessive nociception, and neuropathic and mixed pain.

The pharmaceutical compositions according to the present invention can be formulated for administration to humans. These compositions are produced such that they can be administered by oral, sublingual, subcutaneous, intramuscular, intravenous, transdermal, local or rectal route. In this case, the active ingredient can be administered in administration unit forms, mixed with conventional pharmaceutical supports, to human beings. Suitable administration unit forms include forms by oral route such as tablets, capsules, powders, granules and oral solutions or suspensions, sublingual and buccal forms of administration, subcutaneous, topical, intramuscular, intravenous, intranasal or intraocular forms of administration and rectal forms of administration.

Advantageously, the pharmaceutical composition according to the present invention is formulated for administration by oral or topical route. Administration by topical route is the preferred route for the treatment of certain types of pain, such as for example joint pain.

The term topical administration refers to local administration to the skin or mucous membrane.

Suitable formulations for the administration form chosen are known to the person skilled in the art and are described for example in: Remington, *The Science and Practice of Pharmacy*, $19^{th}$ edition, 1995, Mack Publishing Company.

When a solid composition in the form of tablets is prepared, the principle active ingredient is mixed with a pharmaceutical carrier such as gelatine, starch, lactose, magnesium stearate, talc, gum *arabica*, silica or similar. The tablets can be coated with saccharose or other appropriate materials, or they can be treated such that they have prolonged or delayed activity and release a predetermined amount of active principle in a continuous manner.

A capsule preparation is obtained by mixing the active ingredient with a diluent and pouring the mixture obtained into soft or hard capsules.

A preparation in the form of a syrup or elixir can contain the active ingredient along with a sweetener and an antiseptic, as well as a flavouring agent and a suitable dye.

Powders or granules that are dispersible in water can contain the active ingredient mixed with dispersing agents or wetting agents, or suspending agents, as well as with flavour correctors or sweeteners.

For rectal administration, suppositories are used which are prepared with binding agents that dissolve at rectal temperature, for example cocoa butter or polyethylene glycols.

For parenteral (intravenous, intramuscular, intradermal, subcutaneous), intranasal or intraocular administration, aqueous suspensions, isotonic saline solutions or sterile and injectable solutions are used which contain dispersing agents and/or pharmacologically compatible wetting agents.

The active ingredients can also be formulated as microcapsules, possibly with one or more additive supports if necessary.

Topical administration of the pharmaceutical composition can be obtained by application of a solution, dispersion, gel, lotion, milk, ointment, salve cream, drops or other carrier used for topical application and well known to the person skilled in the art. One possible method is the administration of the pharmaceutical composition by means of an aerosol spray allowing fine liquid droplets to be sprayed for distribution over the entire surface to be treated or, to the contrary, to restrict this precisely to a particular zone to be treated, or in a solid form such as a stick. Another example is a patch or strip which allows continuous release of the topical composition. The patch can be a reservoir and a porous membrane or solid matrix well known to the person skilled in the art. Other modes of administration such as iontophoresis or electroporation can also be used.

The compositions described in this invention can also include ingredients or compounds usually mixed with such topical preparations, for example the compositions can also include additional ingredients such as carriers, moisturisers, oils, fats, waxes, surfactants, thickening agents, antioxidants, viscosity stabilisers, chelating agents, buffers, preservatives, perfumes, colorants, humectants, emollients, dispersing agents, sun creams with compounds blocking radiation and particularly UV blockers, antibacterials, antifungals, disinfectants, vitamins, antibiotics or other anti-acne agents, as well as other adapted substances with no harmful adverse effect on the activity of the topical composition. For example, additional ingredients can be used such as sodium acid phosphate, witch hazel extract, glycerine, apricot kernel oil, maize oil. In addition to the compounds described above, compositions of the present invention can optionally contain other ingredients. For example triethanolamine can be added as a reticulating agent. A preservative such as butylated hydroxytoluene can also be added. Other irritation reducing agents can also be added; in this respect this includes but is not limited to glycerol. For topical administration, the compositions can contain conventional emollients and emulsifiers including alginates, glyceryl stearate, PEG-100 stearate, ketyl alcohol, propylparaben, butylparaben, sorbitols, ethoxylated anhydrosorbitol monostearate (TWEEN), white petrolatum (Vaseline), triethaolamine, emu oil, aloe vera, lanolin, cocoa butter and other extracts.

The compositions described can be applied to the patient's skin area to be treated. The frequency of application will depend on circumstances and the patient. For example the compositions can be applied daily, twice a day or even more frequently.

The doses of a compound of general formula (1) or one of its pharmaceutically acceptable salts in the composition of the invention can be adjusted in order to obtain a quantity of substance that is effective in achieving the desired therapeutic response for a composition specific to the administration method. The effective dose of the compound of the invention varies as a function of numerous parameters such as, for example, the administration route chosen, weight, age, sex, type of disease, sensitivity of the individual to be treated. Consequently the optimum dosage can be established by the specialists in the field as a function of parameters the specialist considers to be relevant. Although the effective doses can vary within broad proportions, the daily doses can be scaled between 1 mg and 1000 mg per 24 h for an adult of average weight of 70 kg, in one or more divided doses.

Finally the invention includes the method for synthesis of products of the compounds of general formula (1) as well as those of synthesis intermediates of formula (C) and (D).

The compounds of general formula (1) can be obtained by the process described in the reaction diagram hereafter.

Reaction Diagram

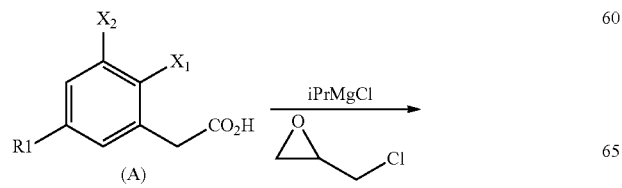

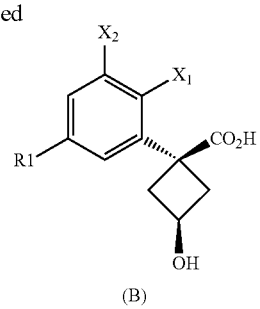

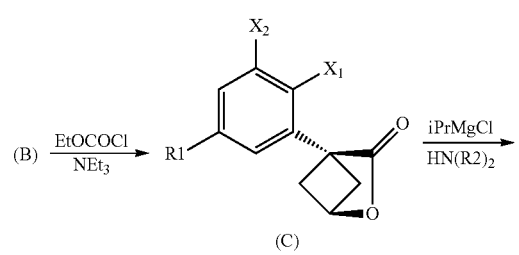

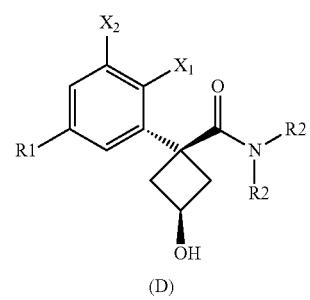

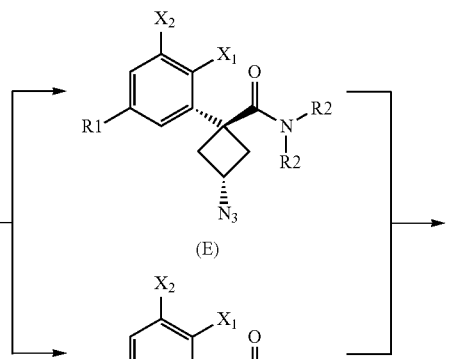

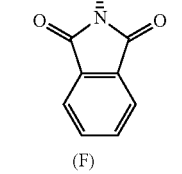

-continued

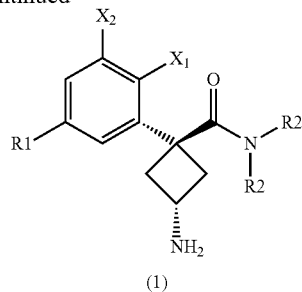

(1)

The preparation of the compounds of the invention uses as starting material derivatives of benzeneacetic acid of formula (A) that are commercially available such as: benzeneacetic acid (RN 103-82-2); 2-fluorobenzene-acetic acid (RN 451-82-1); 3-fluorobenzeneacetic acid (RN 331-25-9); 3-chlorobenzeneacetic acid (RN 1878-65-5); 3-methylbenzeneacetic acid (RN 621-36-3); 3-cyanobenzeneacetic acid (RN 1878-71-3); 3-methoxybenzeneacetic acid (RN 1798-09-0); 2,5-difluorobenzeneacetic acid (RN 85068-27-5); 3,5-difluorobenzeneacetic acid (RN 105184-38-1); 3,5-dichlorobenzeneacetic acid (RN 51719-65-4); 2-fluoro-3-chlorobenzeneacetic acid (RN 261762-96-3). The derivatives of formula (A) are condensed with epichlorhydrin according to a method adapted from that described in patent application WO 2007/038452 to give derivatives of formula (B) in which the alcohol and carboxylic acid groups show 'cis' stereochemistry. Said patent does not describe the intermediates of formula (B). The lactones of formula (C) are then formed from derivatives of formula (B) by using a conventional method of activation of the acid group, for example such as using an alkyl chloroformiate as described in application WO 2008/092955. Opening of the lactone of formula (C) is then advantageously carried out using the magnesium salt of the appropriate secondary amine according to Williams et al. (*Tetrahedron Lett.*, 1995, 36, 5461-5464) to produce the corresponding carboxamide of formula (D). Introduction of the primary amine group in position 3 of cyclobutane with inversion of the stereochemistry can be achieved through the intermediate of the azide of formula (E) according to Soltani Rad et al. (*Tetrahedron Lett.*, 2007, 48, 3445-3449). Reduction of the azido group to the corresponding primary amine is then achieved either by catalytic hydrogenation or by a Staudinger reaction. Alternatively conversion of the compound of formula (D) into the amine of formula (1) can be carried out through the intermediate of phthalimide of formula (F) according to Gabriel's conventional method (for example application WO 2006081179).

The following examples illustrate the invention without being limiting. In the examples below:

(i) different crystalline shapes can give rise to different melting points; the melting points reported in this application are those of the products prepared according to the methods described and are not corrected;

(ii) the structure of the products obtained according to the invention is confirmed by the nuclear magnetic resonance (NMR) spectra and by mass spectrometry; the purity of the final product is verified by TLC and centesimal analysis;

(iii) the NMR spectra are recorded in the solvent given: chemical shifts (δ) are expressed in parts per million (ppm) relative to tetramethylsilane; the multiplicity of signals is indicated by: s, singulet; d, doublet; t, triplet; q, quadruplet; qu, quintuplet; m, multiplet; 1, large;

(iv) the different symbols for units have their usual meaning: μg (microgram); mg (milligram); g (gram); mL (millilitre); mV (millivolt); ° C. (degrees Celsius); mmol (millimole; nmol (nanomol); cm (centimetre); nm (nanometre); min (minute); ms (millisecond), Hz (hertz);

(v) the abbreviations have the following meaning: Mp (melting point); Bp (boiling point);

(vi) the term "ambient temperature", refers to a temperature between 20° C. and 25° C.

EXAMPLE 1 trans-3-amino-N,N-diethyl-1-phenylcyclobutanecarboxamide (1a1)

Step 1:
cis-1-phenyl-3-hydroxy-cyclobutanecarboxylic acid (B1)

Place 2.2 eq of isopropylmagnesium chloride in a three-necked flask and cool the reaction medium to 0° C. Add 1 eq of phenylacetic acid diluted in THF; the temperature must be kept between 40 and 50° C. Cool the medium to 20° C. and add 1.8 eq of epichlorhydrin; the temperature must be kept between 20 and 25° C., and stir at this temperature for 45 min. Next, add 2 eq of isopropylmagnesium chloride (2M in THF) dropwise and stir at room temperature for 2 h. Next heat the reaction medium to 60° C. for 19 h. Allow the medium to cool then acidify with an HCl solution (1N) to pH 1. Add dichloromethane (DCM) and extract. Decant, dry the organic phase over $MgSO_4$, then evaporate the DCM under reduced pressure. Purify the residue by flash chromatography with the following eluent: DCM, then DCM/methanol 70:30. The title product is obtained in the form of a pale yellow solid (yield=70%).

$C_{11}H_{12}O_3$ (molecular weight=192).

$^1$H-NMR (DMSO $d_6$, 400 MHz) δ (ppm): 2.50 (m, 2H), 2.74 (t, 2H, J=9.4 Hz), 3.32 (s, 1H), 3.85 (qu, 1H, J=7.2 Hz), 7.22-7.38 (m, 5H), 12.21 (s, 1H).

SM-ESI: 193.1 (MH$^+$).

Step 2: 4-phenyl-2-oxabicyclo[2.1.1]hexane-3-one (C1)

Place 1 eq of compound B1) in a flask, dilute in THF and 1.03 eq of triethylamine. Stir at room temperature until dissolved then cool the reaction medium to 0° C. Add 1 eq of ethyl chloroformiate and stir at this temperature for 1 h then bring back to room temperature and stir for 20 h. Evaporate THF under reduced pressure, take up the residue with ethyl acetate (AcOEt). Decant, dry the acetate on $MgSO_4$, then evaporate under reduced pressure. Purify the residue by flash chromatography with the following eluant: heptane, then heptane/AcOEt 60:40. The title product is obtained in the form of a colourless oil (yield=87%).

$C_{11}H_{10}O_2$ (MW=174).

$^1$H-NMR (CDCl$_3$, 400 MHz) δ (ppm): 2.71 (m, 2H), 2.89 (m, 2H), 4.97 (s, 1H), 7.31-7.42 (m, 5H).

SM-ESI: 175 (MH$^+$).

Step 3: cis-3-hydroxy-N,N-diethyl-1-phenylcyclobutanecarboxamide (D1a)

Place 1 eq of compound (C1), 2 eq of diethylamine and THF in a three-necked flask. Cool the reaction medium to −20° C., then add 3 eq of isopropylmagnesium chloride dropwise (2M in THF) keeping the temperature below −5°

C. Stir the mixture for 2 h at a temperature between −10 and −20° C. Hydrolyze the reaction medium with a saturated NaCl solution then add an HCl solution (1N) and extract with AcOEt. Dry the organic phase over $MgSO_4$, filter and concentrate. Purify the residue by flash chromatography with the following mixture as the eluant: DCM/methanol 85:15. The title product is obtained in the form a pale yellow solid (yield=99%).

$C_{15}H_{21}NO_2$ (MW=247).

$^1$H-NMR (CDCl$_3$, 400 MHz) δ (ppm): 0.63 (t, 3H, J=7.2 Hz), 1.08 (t, 3H, J=7.2 Hz), 2.72 (m, 2H), 2.82 (m, 2H), 2.90 (q, 2H, J=7.2 Hz), 3.21 (q, 2H, J=7.2 Hz), 4.36 (qu, 1H, J=7.4 Hz), 7.21-7.36 (m, 5H). The signal corresponding to the H in OH is not visible on the spectrum.

SM-ESI: 248 (MH$^+$).

Step 4: trans-3-azido-N,N-diethyl-1-phenylcyclobutanecarboxamide (E1a)

Place 1 eq of compound (D1a), 1.5 eq of N-(p-toluenesulfonyl)imidazole, 2 eq of triethylamine, 0.025 eq of tetrabutylammonium iodide, 3 eq of sodium azide and DMF in a flask. Stir and heat the reaction medium at 160° C. for 4 h. Pour the reaction medium onto ice water and extract with ethyl ether. Dry the organic phase over $MgSO_4$, filter and concentrate. Purify the residue by flash chromatography with the following mixture as the eluant: heptane/AcOEt 70:30. The title product is obtained in the form of a colourless oil (yield=65%).

$C_{15}H_{20}N_4O$ (MW=272).

$^1$H-NMR (CDCl$_3$, 400 MHz) δ (ppm): 0.52 (t, 3H, J=7.2 Hz), 1.11 (t, 3H, J=7.2 Hz), 2.47 (m, 2H), 2.89 (q, 2H, J=7.2 Hz), 3.14 (m, 2H), 3.34 (q, 2H, J=7.2 Hz), 3.96 (qu, 1H, J=7.8 Hz), 7.23 (m, 3H), 7.35 (m, 2H).

SM-ESI: 273 (M+H$^+$).

Step 5: trans-3-amino-N,N-diethyl-1-phenylcyclobutanecarboxamide (1a1)

Dissolve 1 eq of compound (E1a) in methanol in a flask. Degas the solution for 30 min with nitrogen then add Pd/C (20% weight). Purge the system (cycle: vacuum/H$_2$ gas) and hydrogenate the reaction medium for 3 h at room temperature with stirring. Filter the catalyst and evaporate the solvent. Purify the residue by flash chromatography with the following mixture as the eluant: DCM/methanol/NH$_4$OH: 90:9:1. The title product is obtained in the form of a colourless oil (yield=70%).

$C_{15}H_{22}N_2O$ (MW=246).

$^1$H-NMR (DMSO d$_6$, 400 MHz) δ (ppm): 0.50 (t, 3H, J=7.2 Hz), 1.10 (t, 3H, J=7.2 Hz), 2.11 (m, 2H), 2.92 (q, 2H, J=6.8 Hz), 3.12 (m, 2H), 3.32 (q, 2H, J=6.8 Hz), 3.46 (qu, 1H, J=8.0 Hz), 7.18-7.35 (m, 5H). The signal corresponding to the H in NH$_2$ is not visible on the spectrum.

SM-ESI: 247 (MH$^+$).

Maleate of the Title Compound

Salification of the previous compound by means of maleic acid leads to obtaining Maleate of the title compound in the form of a white powder.

Mp: 185° C.

$^1$H-NMR (DMSO d$_6$, 400 MHz) δ (ppm): 0.42 (t, 3H, J=7.0 Hz), 1.02 (t, 3H, J=7.0 Hz), 2.56 (m, 2H), 2.85-2.96 (m, 4H), 3.25 (q, 2H, J=6.8 Hz), 3.54 (qu, 1H, J=8.4 Hz), 6.03 (s, 2H), 7.26 (m, 3H), 7.39 (t, 2H, J=7.6 Hz), 8.00 (s, 2H). The signal corresponding to the H in NH2 is not visible on the spectrum.

$^{13}$C-NMR (DMSO d$_6$, 100 MHz) δ (ppm): 12.02, 12.15, 36.93, 39.19, 40.07, 41.19, 46.61, 124.87, 126.51, 128.71, 136.02, 142.69, 167.19, 171.10.

% Theoretical: C, 62.97; H, 7.23; N, 7.73.
% Found: C, 63.00; H, 7.17; N, 7.78.

EXAMPLE 2 trans-3-amino-N,N-dimethyl-1-phenylcyclobutanecarboxamide (1a2)

Step 3: cis-3-hydroxy-N,N-dimethyl-1-phenylcyclobutanecarboxamide (D1b)

Identical to step 3 described in Example 1, using dimethylamine instead of diethylamine. The title product is obtained in the form of a colourless oil (yield=89%).

$^1$H-NMR (CDCl$_3$, 400 MHz) δ (ppm): 2.65 (m, 2H), 2.55 (s, 3H), 2.95 (s, 3H), 2.80 (m, 2H), 4.27 (qu, 1H, J=7.8 Hz), 7.19-7.35 (m, 5H). The signal corresponding to the H in OH is not visible on the spectrum.

Step 4: trans-3-azido-N,N-dimethyl-1-phenylcyclobutanecarboxamide (E1b)

Identical to step 4 described in Example 1. The title product is obtained in the form of a beige solid (yield=95%).

$^1$H-NMR (CDCl$_3$, 400 MHz) δ (ppm): 2.50 (m, 2H), 2.54 (s, 3H), 2.96 (s, 3H), 3.18 (m, 2H), 3.97 (qu, 1H, J=7.8 Hz), 7.24 (m, 3H), 7.36 (m, 2H).

Step 5: trans-3-amino-N,N-dimethyl-1-phenylcyclobutanecarboxamide (1a2)

Identical to step 5 described in Example 1. The title product is obtained in the form of a colourless oil (yield=84%).

$C_{13}H_{18}N_2O$ (MW=218).

$^1$H-NMR (CDCl$_3$, 400 MHz) δ (ppm): 2.13 (m, 2H), 2.55 (s, 3H), 2.95 (s, 3H), 3.15 (m, 2H), 3.47 (qu, 1H, J=7.8 Hz), 7.19-7.35 (m, 5H). The signal corresponding to the H in NH$_2$ is not visible on the spectrum.

SM-ESI: 219 (MH$^+$).

Maleate of the Title Compound

Salification of the previous compound by means of maleic acid leads to obtaining Maleate of the title compound in the form of a white powder.

Mp: 163° C.

$^1$H-NMR (DMSO d$_6$, 400 MHz) δ (ppm): 2.51 (m, 5H), 2.86 (s, 3H), 2.98 (m, 2H), 3.36 (s, 1H), 3.53 (qu, 1H, J=8.4 Hz), 6.03 (s, 2H), 7.26 (m, 3H), 7.39 (t, 2H, J=7.6 Hz), 8.05 (s, 3H).

$^{13}$C-NMR (DMSO d$_6$, 100 MHz) δ (ppm): 35.80, 37.20, 37.34, 39.91, 46.54, 124.94, 126.59, 128.72, 136.00, 142.43, 167.15, 171.68.

% Theoretical: C, 61.07; H, 6.63; N, 8.38.
% Found: C, 60.73; H, 6.43; N, 8.15.

EXAMPLE 3 trans-3-amino-N,N-diethyl-1-(2-fluorophenyl)-cyclobutanecarboxamide (1b)

Step 1: cis-3-hydroxy-1-(2-fluorophenyl)-cyclobutanecarboxylic acid (B2)

Identical to step 1 described in 1, by using 2-fluorophenylacetic acid as the starting product. The title product is obtained in the form of a white solid (yield=49%).

$C_{11}H_{11}FO_3$ (MW=210).

¹H-NMR (CDCl₃, 400 MHz) δ (ppm): 2.80 (m, 2H), 2.97 (m, 2H), 4.29 (qu, 1H, J=6.4 Hz), 7.04-7.23 (m, 4H). The signals corresponding to the H in OH in the alcohol and acid are not visible on the spectrum.

SM-ESI: 211 (MH⁺).

Step 2:
4-(2-fluorophenyl)-2-oxabicyclo[2.1.1]hexane-3-one (C2)

Identical to step 2 described in Example 1. The title product is obtained in the form of a colourless oil (yield=81%).

$C_{11}H_9FO_2$ (MW=192).

¹H-NMR (CDCl₃, 400 MHz) δ (ppm): 2.75 (m, 2H), 2.99 (m, 2H), 5.01 (s, 1H), 7.07-7.42 (m, 4H).

SM-ESI: =193 (MH⁺).

Step 3: cis-3-hydroxy-N,N-diethyl-1-(2-fluorophenyl)-cyclobutanecarboxamide (D2a)

Identical to step 3 of Example 1. The title product is obtained in the form of a white solid (yield=85%).

$C_{15}H_{20}NO_2F$ (MW=265).

¹H-NMR (CDCl₃, 400 MHz) δ (ppm): 0.47 (t, 3H, J=6.8 Hz), 1.10 (t, 3H, J=6.8 Hz), 2.77-2.89 (m, 4H), 2.95 (m, 2H), 3.31 (m, 2H), 4.32 (qu, 1H, J=6.8 Hz), 7.04 (t, 1H, J=7.8 Hz), 7.15 (t, 1H, J=7.8 Hz), 7.26 (m, 1H), 7.37 (t, 1H, J=7.8 Hz). The signal corresponding to the H in OH is not visible on the spectrum.

SM-ESI: 266 (MH⁺).

Step 4: trans-3-azido-N,N-diethyl-1-(2-fluorophenyl)-cyclobutanecarboxamide (E2a)

Identical to step 4 described in 1. The title product is obtained in the form of a colourless oil (yield=75%).

$C_{15}H_{19}N_4OF$ (MW=290).

¹H-NMR (CDCl₃, 400 MHz) δ (ppm): 0.42 (t, 3H, J=7.0 Hz), 1.10 (t; 3H, J=7.0 Hz), 2.55 (m, 2H), 2.98 (q, 2H, J=7.0 Hz), 3.19 (m, 2H), 3.31 (q, 2H, J=7.0 Hz), 4.02 (qu, 1H, J=8.0 Hz), 7.03 (m, 1H), 7.14-7.29 (m, 3H).

SM-ESI: 291 (MH⁺).

Step 5: trans-3-amino-N,N-diethyl-1-(2-fluorophenyl)-cyclobutanecarboxamide (1b)

Identical to step 5 described in example 1. The title product obtained is in the form of a colourless oil (yield=90%).

$C_{15}H_{21}N_2OF$ (MW=264).

¹H-NMR (CDCl₃, 400 MHz) δ (ppm): 0.42 (t, 3H, J=6.8 Hz), 1.10 (t, 3H, J=6.8 Hz), 2.19 (m, 2H), 3.00 (q, 2H, J=6.8 Hz), 3.17 (m, 2H), 3.31 (q, 2H, J=6.8 Hz), 3.53 (qu, 1H, J=8.0 Hz), 7.00 (m, 1H), 7.11-7.31 (m, 3H). The signal corresponding to the H in NH₂ is not visible on the spectrum.

SM-ESI: 265 (MH⁺).

Maleate of the Title Compound.

Salification of the previous compound by means of maleic acid leads to obtaining Maleate of the title compound in the form of a white powder.

Mp: 193° C.

¹H-NMR (DMSO d₆, 400 MHz) δ (ppm): 0.01 (t, 3H, J=6.8 Hz), 0.77 (t, 3H, J=6.8 Hz), 2.36 (m, 2H), 2.72 (m, 4H), 2.97 (q, 2H, J=6.8 Hz), 3.22 (s, 1H), 3.38 (qu, 1H, J=8.0 Hz), 5.81 (s, 2H), 6.94 (m, 1H), 7.04-7.14 (m, 2H), 7.33 (m, 1H), 7.75 (s, 3H).

¹³C-NMR (DMSO d₆, 100 MHz) δ (ppm): 12.00, 12.20, 36.14, 39.97, 40.60, 41.19, 43.60, 115.71 (d, $^2J_{C-F}$=21 Hz), 124.64 (d, $^4J_{C-F}$=4 Hz), 128.00 (d, $^3J_{C-F}$=5 Hz), 128.80 (d, =8 Hz), 130.07 (d, $^2J_{C-F}$=13 Hz), 136.04, 158.52, 160.96, 167.14, 169.93.

% Theoretical: C, 59.99; H, 6.62; N, 7.36.
% Found: C, 60.15; H, 6.48; N, 7.20.

EXAMPLE 4 trans-3-amino-N,N-diethyl-1-(3-fluorophenyl)-cyclobutanecarboxamide (1c)

Step 1: cis-3-hydroxy-1-(3-fluorophenyl)-cyclobutanecarboxylic acid (B3)

Identical to step 1 of Example 1 by using 3-fluorophenylacetic acid as the starting acid. The title product is obtained in the form of a white solid (yield=52%).

$C_{11}H_{11}FO_3$ (MW=210).

¹H-NMR (DMSO d₆, 400 MHz) δ (ppm): 2.50 (m, 2H), 2.75 (m, 2H), 3.86 (qu, 1H, J=7.2 Hz), 5.18 (s, 1H), 7.07-7.21 (m, 3H), 7.40 (m, 1H), 12.40 (s, 1H).

SM-ESI: 211 (MH⁺).

Step 2:
4-(3-fluorophenyl)-2-oxabicyclo[2.1.1]hexane-3-one (C3)

Identical to step 2 described in Example 1. The title product is obtained in the form of a colourless oil (yield=91%).

$C_{11}H_9O_2F$ (MW=192).

¹H-NMR (DMSO d₅, 400 MHz) δ (ppm): 2.83 (s, 4H), 5.09 (s, 1H), 7.15-7.22 (m, 3H), 7.38-7.47 (m, 1H).

SM-ESI: 193 (MH⁺).

Step 3: cis-3-hydroxy-N,N-diethyl-1-(3-fluorophenyl)-cyclobutanecarboxamide (D3a)

Identical to step 3 of Example 1. The title product is obtained in the form of a white solid (yield=92%).

$C_{15}H_{20}NO_2F$ (MW=265).

¹H-NMR (DMSO d₆, 400 MHz) δ (ppm): 0.62 (t, 3H, J=7.2 Hz), 0.97 (t, 3H, J=7.2 Hz), 2.50 (m, 2H), 2.66 (m, 2H), 2.86 (q, 2H, J=7.2 Hz), 3.19 (q, 2H, J=7.2 Hz), 4.05 (m, 1H), 5.12 (d, 1H, J=6.8 Hz), 7.04-7.15 (m, 3H), 7.39 (m, 1H).

SM-ESI: 266 (MH⁺).

Step 4: trans-3-azido-N,N-diethyl-1-(3-fluorophenyl)-cyclobutanecarboxamide (E3a)

Identical to step 4 described in 1. The title product is obtained in the form of a colourless oil (yield=72%).

¹H-NMR (DMSO d₆, 400 MHz) δ (ppm): 0.59 (t, 3H, J=7.2 Hz), 1.00 (t, 3H, J=7.2 Hz), 2.40 (m, 2H), 2.86 (q, 2H, J=7.2 Hz), 3.04 (m, 2H), 3.24 (q, 2H, J=7.2 Hz), 4.07 (m, 1H), 7.04-7.15 (m, 3H), 7.39 (m, 1H).

Step 5: trans-3-amino-N,N-diethyl-1-(3-fluorophenyl)-cyclobutanecarboxamide (1c)

Identical to step 5 described in Example 1. The title product is obtained in the form of a colourless oil (yield=93%).

$C_{15}H_{21}N_2OF$ (MW=264).

SM-ESI: 265 (MH⁺).

Maleate of the Title Compound

Salification of the previous compound by means of maleic acid leads to obtaining Maleate of the title compound in the form of a white powder.

Mp: 174° C.

$^1$H-NMR (DMSO d$_6$, 400 MHz) δ (ppm): 0.49 (t, 3H, J=7.0 Hz), 1.02 (t, 3H, J=7.0 Hz), 2.56 (m, 2H), 2.91 (m, 4H), 3.26 (q, 2H, J=7.0 Hz), 3.35 (s, 1H), 3.53 (qu, 1H, J=8.4 Hz), 6.03 (s, 2H), 7.01 (d, 1H, J=8.0 Hz), 7.09-7.20 (m, 2H), 7.42 (m, 1H), 7.99 (s, 3H).

$^{13}$C-NMR (DMSO d$_6$, 100 MHz) δ (ppm): 12.10, 36.93, 39.23, 39.91, 41.18, 46.40, 111.03 (d, $^2J_{C-F}$=22 Hz), 113.39 (d, $^2J_{C-F}$=21 Hz), 121.11 (d, $^4J_{C-F}$=2 Hz), 130.77 (d, $^3J_{C-F}$=9 Hz), 136.02, 145.55 (d, 7 Hz), 161.21, 163.64, 167.14, 170.60.

% Theoretical: C, 59.99; H, 6.62; N, 7.36.

% Found: C, 59.11; H, 6.40; N, 7.07.

EXAMPLE 5 trans-3-amino-N,N-diethyl-1-(3-methoxyphenyl)-cyclobutanecarboxamide (1d)

Step 1: cis-3-hydroxy-1-(3-methoxyphenyl)-cyclobutanecarboxylic acid (B4)

Identical to step 1 of Example 1 by using 3-methoxyphenylacetic instead of phenylacetic acid. The title product is obtained in the form of a white solid (yield=50%).

$C_{12}H_{14}O_4$ (MW=222).

$^1$H-NMR (DMSO d$_6$, 400 MHz) δ (ppm): 2.50 (m, 2H), 2.73 (m, 2H), 3.75 (s, 3H), 3.86 (qu, 1H, J=7.2 Hz), 5.14 (s, 1H), 6.82 (dd, 1H, J=8.0 Hz and J=2.0 Hz), 6.87 (s, 1H), 6.93 (d, 1H, J=8.0 Hz), 7.26 (t, 1H, J=8.0 Hz), 12.23 (s, 1H).

SM-ESI: 222.

Step 2: 4-(3-methoxyphenyl)-2-oxabicyclo[2.1.1]hexane-3-one (C4)

Identical to step 2 described in Example 1. The title product is obtained in the form of a colourless oil (yield=85%).

$C_{12}H_{12}O_2$ (MW=188).

$^1$H-NMR (DMSO d$_6$, 400 MHz) δ (ppm): 2.80 (m, 4H), 3.76 (s, 3H), 5.06 (s, 1H), 6.87-6.91 (m, 3H), 7.30 (t, 1H, J=8.0 Hz).

SM-ESI: 189 (MH$^+$).

Step 3: cis-3-hydroxy-N,N-diethyl-1-(3-methoxyphenyl)-cyclobutanecarboxamide (D4a)

Identical to step 3 described for Example 1. The title product is obtained in the form of a white solid (yield=92%).

$C_{16}H_{23}NO_3$ (MW=277)

$^1$H-NMR (DMSO d$_6$, 400 MHz) δ (ppm): 0.62 (t, 3H, J=6.8 Hz), 0.97 (t, 3H, J=6.8 Hz), 2.50 (m, 2H), 2.64 (m, 2H), 2.86 (q, 2H, J=6.8 Hz), 3.19 (q, 2H, J=6.8 Hz), 3.73 (s, 3H), 4.06 (se, 1H, J=7.6 Hz), 5.08 (d, 1H, J=7.2 Hz), 6.81 (m, 2H), 6.89 (d, 1H, J=7.6 Hz), 7.27 (m, 1H).

SM-ESI: 278 (MH$^+$).

Step 4: trans-3-azido-N,N-diethyl-1-(3-methoxyphenyl)-cyclobutanecarboxamide (E4a)

Identical to step 4 described for Example 1. The title product is obtained in the form of a colourless oil (yield=82%).

$C_{16}H_{22}N_4O_2$ (MW=302).

$^1$H-NMR (DMSO d$_6$, 400 MHz) δ (ppm): 0.59 (t, 3H, J=6.8 Hz), 1.00 (t, 3H, J=6.8 Hz), 2.40 (m, 2H), 2.86 (q, 2H, J=6.8 Hz), 3.05 (m, 2H), 3.24 (q, 2H, J=6.8 Hz), 3.74 (s, 3H), 3.95 (qu, 1H, J=7.6 Hz), 6.76 (m, 1H), 6.83 (m, 2H), 7.30 (m, 1H).

SM-ESI: 303 (MH$^+$).

Step 5: trans-3-amino-N,N-diethyl-1-(3-methoxyphenyl)-cyclobutanecarboxamide (1d)

Identical to step 5 described for Example 1. The title product is obtained in the form of a colourless oil (yield=88%).

$C_{16}H_{24}N_2O_2$ (MW=276).

$^1$H-NMR (DMSO d$_6$, 400 MHz) δ (ppm): 0.50 (t, 3H, J=7.0 Hz), 1.00 (t, 3H, J=7.0 Hz), 2.02 (m, 2H), 2.83 (m, 4H), 3.10 (qu, 1H, J=8.0 Hz), 3.23 (q, 2H, J=7.2 Hz), 3.33 (s, 2H), 3.73 (s, 3H), 6.73-6.79 (m, 3H), 7.25 (t, 1H, J=8.0 Hz).

SM-ESI: 277 (MH$^+$).

Maleate of the Title Compound

Salification of the previous compound by means of maleic acid leads to obtaining Maleate of the title compound in the form of a white powder.

Mp: 156° C.

$^1$H-NMR (DMSO d$_6$, 400 MHz) δ (ppm): 0.47 (t, 3H, J=6.8 Hz), 1.02 (t, 3H, J=6.8 Hz), 2.55 (m, 2H), 2.89 (m, 4H), 3.26 (q, 2H, J=6.8 Hz), 3.35 (s, 1H), 3.52 (qu, 1H, J=8.4 Hz), 3.75 (s, 3H), 6.03 (s, 2H), 6.78-6.86 (m, 3H), 7.31 (t, 1H, J=8.0 Hz), 7.98 (s, 3H).

$^{13}$C-NMR (DMSO d$_6$, 100 MHz) δ (ppm): 12.11, 36.98, 39.23, 39.99, 41.23, 46.57, 55.03, 111.05, 111.54, 117.12, 129.89, 136.03, 144.22, 159.54, 167.12, 171.02.

% Theoretical: C, 61.21; H, 7.19; N, 7.14.

% Found: C, 61.38; H, 7.09; N, 6.98.

EXAMPLE 6 trans-3-amino-N,N-diethyl-1-(3-chlorophenyl)-cyclobutanecarboxamide (1e)

Step 1: cis-3-hydroxy-1-(3-chlorophenyl)-cyclobutanecarboxylic acid (B5)

Identical to step 1 described in 1 by using 3-chlorophenylacetic acid as the starting acid. The title compound is obtained in the form of a white solid (yield=52%).

$C_{11}H_{11}O_3Cl$ (MW=226.5).

$^1$H-NMR (DMSO d$_6$, 400 MHz) δ (ppm): 2.50 (m, 2H), 2.75 (m, 2H), 3.86 (qu, 1H, J=7.2 Hz), 5.19 (s, 1H), 7.31-7.40 (m, 4H), 12.44 (s, 1H).

Step 2: 4-(3-chlorophenyl)-2-oxabicyclo[2.1.1]hexane-3-one (C5)

Identical to step 2 described in Example 1. The title product is obtained in the form of a colourless oil (yield=78%).

$C_{11}H_9O_2Cl$ (MW=208).

$^1$H-NMR (DMSO d$_6$, 400 MHz) δ (ppm): 2.84 (m, 4H), 5.09 (s, 1H), 7.29-7.45 (m, 4H).

SM-ESI: 209 (MH$^+$).

Step 3: cis-3-hydroxy-N,N-diethyl-1-(3-chlorophenyl)-cyclobutanecarboxamide (D5a)

Identical to step 3 described in example 1. The title compound is obtained in the form of a white solid (yield=99%).

$C_{15}H_{20}NO_2Cl$ (MW=281.5).

$^1$H-NMR (DMSO d$_6$, 400 MHz) δ (ppm): 0.63 (t, 3H, J=6.8 Hz), 0.96 (t, 3H, J=6.8 Hz), 2.51 (m, 2H), 2.66 (m, 2H), 2.86 (q, 2H, J=6.8 Hz), 3.19 (q, 2H, J=6.8 Hz), 4.05 (qu, 1H, J=7.6 Hz), 5.13 (s, 1H), 7.29-7.41 (m, 4H).

SM-ESI: 282.1 (MH$^+$).

Step 4: trans-3-(dioxoisoindoline-2-yl)-N,N-diethyl-1-(3-chlorophenyl)-cyclobutanecarboxamide (F5a)

In a flask under an atmosphere of nitrogen, add 1 eq of compound (D5a), 1.1 eq of triphenylphosphine, 1.05 eq of phthalimide and THF. Next, add 1.2 eq of diisopropyldiazodicarboxylate (DIAD) dropwise and stir at room temperature for 16 h. Add water and extract with DCM. Dry the organic phase over Na$_2$SO$_4$, filter and concentrate. Purify the residue by flash chromatography with the following mixture as the eluent: heptane/AcOEt: 80:20. The title product is obtained with a yield de 77%.

$C_{23}H_{23}N_2O_3Cl$ (MW=410.5).

$^1$H-NMR (CDCl$_3$, 400 MHz) δ (ppm): 0.67 (t, 3H, J=7.2 Hz), 1.18 (t, 3H, J=7.2 Hz), 2.91 (q, 2H, J=7.2 Hz), 3.11 (m, 2H), 3.35 (m, 2H), 3.42 (q, 2H, J=7.2 Hz), 4.79 (qu, 1H, J=8.8 Hz), 7.23 (m, 1H), 7.32 (m, 2H), 7.41 (s, 1H), 7.73 (m, 2H), 7.83 (m, 2H).

SM-ESI: 411.1 (MH$^+$).

Step 5: trans-3-amino-N,N-diethyl-1-(3-chlorophenyl)-cyclobutanecarboxamide (1e)

Place derivative (F5a) in solution in ethanolamine in a flask. Heat the reaction medium at 60° C. for 1 h 30. Add a mixture of ice and water, stir for 15 min and extract with AcOEt. Wash the organic phase with saturated NaCl solution and decant. Dry the organic phase over MgSO$_4$, filter and concentrate. Purify the residue by flash chromatography with the following mixture as the eluent: DCM/methanol/NH$_4$OH: 90:9:1. The title product is obtained with a yield de 40%.

$C_{15}H_{21}N_2OCl$ (MW=280.5).

$^1$H-NMR (CDCl$_3$, 400 MHz) δ (ppm): 0.58 (t, 3H, J=7.2 Hz), 1.10 (t, 3H, J=7.2 Hz), 2.08 (m, 2H), 2.91 (q, 2H, J 7.2 Hz), 3.11 (m, 2H), 3.34 (q, 2H, J=7.2 Hz), 3.46 (qu, 1H, J=8.0 Hz), 7.12 (dd, 1H, J=7.6 Hz and J=1.2 Hz), 7.19 (m, 2H), 7.26 (m, 1H). The signal corresponding to the H in NH$_2$ is not visible on the spectrum.

SM-ESI: 281.1 (MH$^+$).

Maleate of the Title Compound

Salification of the previous compound by means of maleic acid leads to obtaining Maleate of the title compound in the form of a white powder.

Mp: 167° C.

$^1$H-NMR (DMSO d$_6$, 400 MHz) δ (ppm): 0.50 (t, 3H, J=6.8 Hz), 1.02 (t, 3H, J=6.8 Hz), 2.56 (m, 2H), 2.86-2.95 (m, 4H), 3.26 (m, 2H), 3.34 (s, 1H), 3.54 (qu, 1H, J=8.0 Hz), 6.03 (s, 2H), 7.15 (d, 1H, J=7.6 Hz), 7.34-7.44 (m, 3H), 8.00 (s, 3H).

$^{13}$C-NMR (DMSO d$_6$. 100 MHz) δ (ppm): 12.09, 12.12, 36.88, 39.19, 39.90, 41.14, 46.37, 123.76, 124.94, 126.61, 130.65, 133.51, 136.00, 145.09, 167.14, 170.54.

% Theoretical: C, 57.50; H, 6.35; N, 7.06.
% Found: C, 57.36; H, 6.26; N, 6.68.

EXAMPLE 7 trans-3-amino-N,N-diethyl-1-(3-methylphenyl)-cyclobutanecarboxamide (1f)

Step 1: cis-3-hydroxy-1-(3-methylphenyl)-cyclobutanecarboxylic acid (B6)

Identical to step 1 of Example 1 by using 3-methylphenylacetic acid instead of phenylacetic acid. The title product is obtained in the form of a white solid (yield=40%).

$C_{12}H_{14}O_3$ (MW=206).

$^1$H-NMR (CDCl$_3$. 400 MHz) δ (ppm): 2.35 (s, 3H), 2.73 (m, 2H), 2.94 (m, 2H), 4.21 (qu, 1H, J=6.4 Hz), 7.08 (d, 1H, J=7.6 Hz), 7.16 (s, 2H), 7.24 (m, 1H). The signals corresponding to the H in OH in the alcohol and acid are not visible on the spectrum.

SM-ESI: 205.

Step 2: 4-(3-methylphenyl)-2-oxabicyclo[2.1.1]hexane-3-one (C6)

Identical to step 2 described in Example 1. The title product is obtained in the form of a colourless oil (yield=74%).

$C_{12}H_{12}O_2$ (MW=188).

$^1$H-NMR (DMSO d$_6$, 400 MHz) δ (ppm): 2.37 (s, 3H), 2.70 (m, 2H), 2.87 (m, 2H), 4.96 (s, 1H), 7.09-7.30 (m, 4H).

SM-ESI: 189 (MH$^+$).

Step 3: cis-3-hydroxy-N,N-diethyl-1-(3-methylphenyl)-cyclobutanecarboxamide (D6a)

Identical to step 3 described in example 1. The title product is obtained with a yield de 77%.

$^1$H-NMR (CDCl$_3$, 400 MHz) δ (ppm): 0.65 (t, 3H, J=7.2 Hz), 1.08 (t, 3H, J=7.2 Hz), 2.69 (s, 3H), 2.73 (m, 2H), 2.81 (m, 2H), 2.90 (q, 2H, J=7.2 Hz), 3.31 (q, 2H, J=7.2 Hz), 4.35 (qu, 1H, J=7.4 Hz), 7.04 (m, 1H), 7.11 (m, 2H), 7.23 (m, 1H). The signal corresponding to the H in OH is not visible on the spectrum.

Step 4: trans-3-azido-N,N-diethyl-1-(3-methylphenyl)-cyclobutanecarboxamide (E6a)

Identical to step 4 described in 1. The title product is obtained with a yield de 70%.

$^1$H-NMR (CDCl$_3$. 400 MHz) δ (ppm): 0.54 (t, 3H, J=7.2 Hz), 1.11 (t, 3H, J=7.2 Hz), 2.34 (s, 3H), 2.47 (m, 2H), 2.89 (q, 2H, J=7.2 Hz), 3.12 (m, 2H), 3.34 (q, 2H, J=7.2 Hz), 3.95 (qu, 1H, J=7.8 Hz), 7.04 (m, 3H), 7.23 (m, 1H).

Step 5: trans-3-amino-N,N-diethyl-1-(3-methylphenyl)-cyclobutanecarboxamide (1f)

Identical to step 5 described in Example 1. The title product is obtained with a yield de 57%.

$C_{16}H_{24}N_2O$ (MW=260).

$^1$H-NMR (CDCl$_3$, 400 MHz) δ (ppm): 0.52 (t, 3H, J=7, 2 Hz), 1.10 (t, 3H, J=7, 2 Hz), 2.11 (m, 2H), 2.33 (s, 3H), 2.92

(q, 2H, J=7.2 Hz), 3.10 (m, 2H), 3.33 (q, 2H, J=7.2 Hz), 3.44 (qu, 1H, J=8.0 Hz), 7.03 (m, 3H), 7.21 (m, 1H). The signal corresponding to the H in $NH_2$ is not visible on the spectrum.
SM-ESI: 261 ($MH^+$).

Maleate of the Title Compound

Salification of the previous compound by means of maleic acid leads to obtaining Maleate of the title compound in the form of a white powder.
Mp: 173° C.
$^1$H-NMR (DMSO $d_6$, 400 MHz) δ (ppm): 0.45 (t, 3H, J=6.8 Hz), 1.02 (t, 3H, J=6.8 Hz), 2.31 (s, 3H), 2.52 (m, 2H), 2.89 (m, 4H), 3.25 (q, 2H, J=6.8 Hz), 3.52 (qu, 1H, J=8.4 Hz), 6.02 (s, 2H), 7.05 (m, 3H), 7.27 (t, 1H, J=7.6 Hz), 8.00 (s, 2H). The signal corresponding to the H in NH2 is not visible on the spectrum.
$^{13}$C-NMR (DMSO $d_6$, 100 MHz) δ (ppm): 12.07, 12.13, 21.05, 36.97, 39.15, 40.09, 41.18, 46.56, 48.53, 121.99, 125.43, 127.15, 128.63, 136.07, 137.88, 142.66, 167.21, 171.19.
% Theoretical: C, 63.81; H, 7.50; N, 7.44.
% Found: C, 63.93; H, 7.45; N, 7.27.

EXAMPLE 8 trans-3-amino-N,N-diethyl-1-(2-fluoro-3-chlorophenyl)-cyclobutanecarboxamide (1g)

Step 1: cis-3-hydroxy-1-(2-fluoro-3-chlorophenyl)-cyclobutanecarboxylic acid (B7)

Identical to step 1 of Example 1 by using 2-fluoro-3-chlorophenylacetic acid instead of phenylacetic acid. The title product is obtained in the form of a white solid (yield=30%).
$C_{11}H_{10}FClO_3$ (MW=244.5).
$^1$H-NMR (DMSO $d_6$, 400 MHz) δ (ppm): 2.58 (m, 2H), 2.75 (m, 2H), 3.93 (qu, 1H, J=7.6 Hz), 5.33 (s, 1H), 7.22 (m, 1H), 7.52 (m, 2H), 12.56 (m, 1H).
SM-ESI: 243.0.

Step 2: 4-(2-fluoro-3-chlorophenyl)-2-oxabicyclo[2.1.1]hexane-3-one (C7)

Identical to step 2 described in Example 1. The title product is obtained in the form of a colourless oil (yield=66%).
$C_{11}H_8O_2ClF$ (MW=226.5).
$^1$H-NMR (DMSO $d_6$, 400 MHz) δ (ppm): 2.89 (s, 4H), 5.16 (s, 1H), 7.22-7.29 (m, 2H), 7.61 (m, 1H).
SM-ESI: 227 ($MH^+$).

Step 3: cis-3-hydroxy-N,N-diethyl-1-(2-fluoro-3-chlorophenyl)-cyclobutanecarboxamide (D7a)

Identical to step 3 described in example 1. The title product is obtained with a yield de 87%.
$C_{15}H_{19}NO_2ClF$ (MW=299.5).
$^1$H-NMR (DMSO $d_6$, 400 MHz) δ (ppm): 0.35 (t, 3H, J=7.0 Hz), 0.96 (t, 3H, J=7.0 Hz), 2.57 (m, 2H), 2.67 (m, 2H), 2.87 (q, 2H, J=7.0 Hz), 3.16 (q, 2H, J=7.0 Hz), 4.00 (se, 1H, J=8.0 Hz), 5.02 (d, 1H, J=7.2 Hz), 7.27 (t, 1H, J=8.0 Hz), 7.50 (t, 1H, J=8.0 Hz), 7.65 (t, 1H, J=8.0 Hz).
SM-ESI: 300 ($MH^+$).

Step 4: trans-3-(dioxoisoindoline-2-yl)-N,N-diethyl-1-(2-fluoro-3-chlorophenyl)-cyclobutanecarboxamide (F7a)

Identical to step 4 described for Example 6. The title product is obtained with a yield de 45%.
$C_{23}H_{22}FClN_2O_3$ (MW=428.5).
$^1$H-NMR ($CDCl_3$, 400 MHz) δ (ppm): 0.29 (t, 3H, J=6.8 Hz), 1.04 (t, 3H, J=6.8 Hz), 2.94-3.04 (m, 4H), 3.22-3.28 (m, 4H), 4.61 (qu, 1H, J=8.8 Hz), 7.35 (t, 1H, J 8.0 Hz), 7.54 (t, 1H, J=8.4 Hz), 7.62 (t, 1H, J=7.2 Hz), 7.83 (s, 4H).
SM-ESI: 429 ($MH^+$).

Step 5: trans-3-amino-N,N-diethyl-1-(2-fluoro-3-chlorophenyl)-cyclobutanecarboxamide (1g)

Identical to step 5 described for Example 6. The title product is obtained with a yield de 93%.
$C_{15}H_{20}FClN_2O$ (MW=298.5).
$^1$H-NMR (DMSO $d_6$, 400 MHz) δ (ppm): 0.27 (t, 3H, J=6.8 Hz), 0.97 (t, 3H, J=6.8 Hz), 2.08 (m, 2H), 2.88-2.94 (m, 4H), 3.17-3.25 (m, 3H), 7.26 (t, 1H, J=8.0 Hz), 7.44-7.49 (m, 2H). The signal corresponding to the H in $NH_2$ is not visible on the spectrum.
SM-ESI: 299 ($MH^+$).

Maleate of the Title Compound

Salification of the previous compound by means of maleic acid leads to obtaining Maleate of the title compound in the form of a white powder.
Mp: 179° C.
$^1$H-NMR (DMSO $d_6$, 400 MHz) δ (ppm): 0.26 (t, 3H, J=6.8 Hz), 0.99 (t, 3H, J=6.8 Hz), 2.60 (m, 2H), 2.91-3.00 (m, 4H), 3.20 (q, 2H, J=6.8 Hz), 3.34 (s, 1H), 3.61 (qu, 1H, J 8.4 Hz), 6.02 (s, 2H), 7.32 (t, 1H, J=8.0 Hz), 7.52-7.57 (m, 2H), 7.97 (s, 3H).
$^{13}$C-NMR (DMSO $d_6$, 100 MHz) δ (ppm): 12.15, 12.21, 36.19, 40.08, 40.56, 41.16, 43.81, 120.16, 125.59, 127.11, 129.12, 132.00, 136.11, 153.74, 156.22, 167.19, 169.48.
% Theoretical: C, 55.01; H, 5.83; N, 6.75.
% Found: C, 54.73; H, 5.98; N, 6.46.

EXAMPLE 9 trans-3-amino-N,N-diethyl-1-(2,5-difluorophenyl)-cyclobutanecarboxamide (1h)

Step 1: cis-3-hydroxy-1-(2,5-difluorophenyl)-cyclobutanecarboxylic acid (B8)

Identical to step 1 described in 1 by using 2,5-difluorophenylacetic acid as the starting acid. The title product is obtained in the form of a white solid (yield=69%).
$^1$H-NMR (DMSO $d_6$, 400 MHz) δ (ppm): 2.55 (m, 2H), 2.71 (m, 2H), 3.94 (qu, 1H, J=7.2 Hz), 5.32 (s, 1H), 7.12-7.23 (m, 2H), 7.41 (m, 1H), 12.48 (s, 1H).

Step 2: 4-(2,5-difluophenyl)-2-oxabicyclo[2.1.1]hexane-3-one (C8)

Identical to step 2 described in Example 1. The title product is obtained in the form of a colourless oil (yield=91%).
$C_{11}H_8F_2O_2$ (MW=210).
$^1$H-NMR ($CDCl_3$, 400 MHz) δ (ppm): 2.77 (m, 2H), 2.98 (m, 2H), 5.01 (s, 1H), 6.93-7.08 (m, 3H).
SM-ESI: 228 ($M+NH_4^+$).

Step 3: cis-3-hydroxy-N,N-diethyl-1-(2,5-difluorophenyl)-cyclobutanecarboxamide (D8a)

Identical to step 3 of Example 1. The title product is obtained in the form of a white solid (yield=100%).
$C_{15}H_{19}NO_2F_2$ (MW=283).

¹H-NMR (CDCl₃, 400 MHz) δ (ppm): 0.56 (t, 3H, J=6.8 Hz), 1.09 (t, 3H, J=6.8 Hz), 2.82 (m, 5H), 2.95 (q, 2H, J=6.8 Hz), 3.31 (q, 2H, J=6.8 Hz), 4.32 (qu, 1H, J=7.2 Hz), 6.91-7.11 (m, 3H).
SM-ESI: 284 (MH⁺).

Step 4: trans-3-azido-N,N-diethyl-1-(2,5-difluorophenyl)-cyclobutanecarboxamide (E8a)

Identical to step 4 described in 1. The title product is obtained in the form of a colourless oil (yield=76%).
$C_{15}H_{18}N_4OF_2$ (MW=308).
¹H-NMR (CDCl₂, 400 MHz) δ (ppm): 0.51 (t, 3H, J=7.2 Hz), 1.10 (t, 3H, J=7, 2 Hz), 2.51 (m, 2H), 2.98 (q, 2H, J=7.2 Hz), 3.19 (m, 2H), 3.32 (q, 2H, J=7.2 Hz), 4.02 (qu, 1H, J=8.0 Hz), 6.90-7.04 (m, 3H),
SM-ESI: 309 (MH⁺).

Step 5: trans-3-amino-N,N-diethyl-1-(2,5-difluorophenyl)-cyclobutanecarboxamide (1h)

Place 1 eq of compound (E8a) in a flask and dissolve in 20 volumes of THF. Stir under an atmosphere of nitrogen then add 1 volume of water and 1.5 eq of triphenylphosphine.
Carry on stirring overnight. Evaporate the THF under reduced pressure and take up the residue obtained with water and extract twice with DCM. Dry the organic phases on MgSO₄, filter then evaporate the solvent under reduced pressure. The oil obtained is purified by flash chromatography with the following mixture as the eluant: DCM/methanol/NH₄OH 95:4.5:0.5. The title product is obtained in the form colourless oil with a yield de 97%.
$C_{15}H_{20}N_2OF_2$ (MW=282).
¹H-NMR (CDCl₃, 400 MHz) δ (ppm): 0.51 (t, 3H, J=6.8 Hz), 1.10 (t, 3H, J=6, 8 Hz), 2.15 (m, 2H), 2.99 (q, 2H, J=6.8 Hz), 3.16 (m, 2H), 3.32 (q, 2H, J=6.8 Hz), 3.52 (qu, 1H, J=8.0 Hz), 6.85-7.02 (m, 3H). The signal corresponding to the H in NH₂ is not visible on the spectrum.
SM-ESI: 283 (MH⁺).
Maleate of the Title Compound
Salification of the previous compound by means of maleic acid leads to obtaining Maleate of the title compound in the form of a white powder.
Mp: 184° C.
¹H-NMR (DMSO d₆, 400 MHz) δ (ppm): 0.31 (t, 3H, J=6.8 Hz), 0.99 (t, 3H, J=6.8 Hz), 2.58 (m, 2H), 2.93-2.97 (m, 4H), 3.20 (q, 2H, J=6.8 Hz), 3.34 (s, 1H), 3.59 (qu, 1H, J=8.4 Hz), 6.02 (s, 2H), 7.13-7.30 (m, 2H), 7.49-7.53 (m, 1H), 7.97 (s, 3H).
¹³C-NMR (DMSO d₆, 100 MHz) δ (ppm): 12.04, 12.15, 36.08, 40.00, 40.61, 41.20, 43.48, 114.90, 117.2, 124.37, 132.1, 136.00, 154.6, 157.05, 157.13, 159.51, 167.12, 169.41.
% Theoretical: C, 57.28; H, 6.07; N, 7.03.
% Found C: 57.21; H, 6.01; N, 6.66.

EXAMPLE 10 trans-3-amino-N,N-diethyl-1-(3,5-dichlorophenyl)-cyclobutanecarboxamide (1i)

Step 1: cis-3-hydroxy-1-(3,5-dichlorophenyl)-cyclobutanecarboxylic acid (B9)

Identical to step 1 described in 1 by synthesizing 3,5-dichlorophenylacetic acid in advance after which it is used as the starting acid. The title product is obtained in the form of a white solid (yield=50%).
$C_{11}H_{10}Cl_2O_3$ (MW=261).
¹H-NMR (DMSO d₆, 400 MHz) δ (ppm): 2.53 (m, 2H), 2.77 (m, 2H), 3.87 (qu, 1H, J=7.4 Hz), 5.23 (s, 1H), 7.38 (m, 2H), 7.51 (m, 1H), 12.62 (s, 1H).
SM-ESI: 259.

Step 2: 4-(3,5-dichlorophenyl)-2-oxabicyclo[2.1.1]hexane-3-one (C9)

Identical to step 2 described in Example 1. The title product is obtained in the form of a colourless oil (yield=87%).
$C_{11}H_8Cl_2O_2$ (MW=243).
¹H-NMR (CDCl₃, 400 MHz) δ (ppm): 2.72 (m, 2H), 2.88 (m, 2H), 4.99 (s, 1H), 7.21 (m, 2H), 7.34 (m, 1H).
SM-ESI: 244 (MH⁺).

Step 3: cis-3-hydroxy-N,N-diethyl-1-(3,5-dichlorophenyl)-cyclobutanecarboxamide (D9a)

Identical to step 3 of Example 1. The title product is obtained in the form of a white solid (yield=100%).
$C_{15}H_{19}Cl_2O_2N$ (MW=316).
¹H-NMR (CDCl₃, 400 MHz) δ (ppm): 0.77 (t, 3H, J=7.2 Hz), 1.09 (t, 3H, J=7.2 Hz), 2.58 (s, 1H), 2.75 (m, 4H), 2.88 (q, 2H, J=7.2 Hz), 3.32 (q, 2H, J=7.2 Hz), 4.34 (qu, 1H, J=7.6 Hz), 7.20-7.27 (m, 3H).
SM-ESI: 316.

Step 4: trans-3-azido-N,N-diethyl-1-(3,5-dichlorophenyl)-cyclobutanecarboxamide (E9a)

Identical to step 4 described in 1. The title product is obtained in the form of a colourless oil (yield=79%).
$C_{15}H_{18}N_4OCl_2$ (MW=341).
¹H-NMR (CDCl₃, 400 MHz) δ (ppm): 0.67 (t, 3H, J=7.2 Hz), 1.12 (t, 3H, J=7.2 Hz), 2.40 (m, 2H), 2.87 (q, 2H, J=7.2 Hz), 3.15 (m, 2H), 3.36 (q, 2H, J=7.2 Hz), 3.99 (qu, 1H, J=7.6 Hz), 7.13 (m, 2H), 7.25 (m, 1H).
SM-ESI: 341.

Step 5: trans-3-amino-N,N-diethyl-1-(3,5-dichlorophenyl)-cyclobutanecarboxamide (1i)

Identical to step 5 of Example 9. The title product is obtained in the form colourless oil with a yield de 78%.
$C_{16}H_{20}N_2OClF$ (MW=283).
¹H-NMR (DMSO d₆, 400 MHz) δ (ppm): 0.58 (t, 3H, J=7.2 Hz), 1.00 (t, 3H, J=7.2 Hz), 1.90 (s, 2H), 2.07 (m, 2H), 2.85 (m, 4H), 3.11 (qu, 1H, J=8.0 Hz), 3.25 (q, 2H, J=7.2 Hz), 7.23 (m, 2H), 7.48 (m, 1H).
SM-ESI: 283.
Maleate of the Title Compound
Salification of the previous compound by means of maleic acid leads to obtaining Maleate of the title compound in the form of a white powder.
Mp: 180° C.
¹H-NMR (DMSO d₆, 400 MHz) δ (ppm): 0.57 (t, 3H, J=6.8 Hz), 1.02 (t, 3H, J=6.8 Hz), 2.58 (m, 2H), 2.85-2.96 (m, 4H), 3.28 (q, 2H, J=6.8 Hz), 3.54 (qu, 1H, J=8.4 Hz), 6.02 (s, 2H), 7.28 (s, 2H), 7.56 (s, 1H), 7.99 (s, 3H).
¹³C-NMR (DMSO d₆, 100 MHz) δ (ppm): 11.96, 12.19, 36.83, 39.20, 41.10, 46.2, 124.03, 126.38, 134.50, 136.02, 146.66, 167.12, 170.04.
% Theoretical: C, 52.91; H, 5.61; N, 6.50.
% Found: C, 53.01; H, 5.53; N, 6.11.

The following examples make it possible to understand the invention better without in any way limiting its scope.

The compounds of general formula (1) as well as a pharmaceutically acceptable source present remarkable pharmacological properties: they are generally more powerful than ketamine as NMDA channel blockers at the same time as having fewer unwanted effects on the central nervous system than ketamine.

We examined the effects of the compounds of the invention on inhibition of the NMDA current in Xenope (*Xenopus laevis*) expressing recombinant human NMDA receptors constructed from NR1 and NR2B sub-units. The currents produced by stimulation of these receptors by means of endogenous agonists were studied according to the two electrode voltage clamp technique reported by Planells-Cases et al., 2002, *J. Pharmacol. Exp. Ther.*, 302, 163-173.

Protocol: ovocytes were surgically removed from adults xenopes, enzymatically defolliculated and stored at 17° C. in a solution containing: 96 mM of NaCl, 2 mM of KCl, 1 mM of $MgCl_2$, 1.8 mM of $CaCl_2$ and 5 mM of HEPES at pH 7.5 (NaOH) and 50 mg/L of gentamycin (Heusler et al., 2005, *Neuropharmacology*, 49, 963-976). Complementary DNA (cDNA) coding for the NR1 sub-unit was cloned by PCR using primers targeted for start and end codons in the published sequence (Genebank access number M_007327). cDNA coding for the NR2B sub-unit was synthesised by Eurogentec (Seraing, Belgium) according to the published sequence (gene bank access number NM_000834). The NR1 and NR2B cDNA was then sub-cloned in the pGEMHE high expression carrier for in vitro transcription of cDNA. cRNA coding for NR1 and NR2B was prepared according to the method described by Heusler et al. (already cited). Aliquots of the cRNA solution were injected into the ovocytes (20-500 pg/ovocyte for NR1 and 40-1000 pg/ovocyte for NR2B). Each ovocyte was injected with 100 nL of a solution containing: 4 mM of $Na^+BAPTA$ (pH 7.2) in order to block all residual chlorine currents. After stabilisation, NMDA currents were activated by superfusion of glutamate and glycine each at a concentration of 10 µM. The compounds to be tested were then superfused in a Ringer $Ba^{++}$ solution at increasing concentrations in the presence of glutamate and glycine (4 to 5 concentrations were tested per ovocyte). The concentration-response codes obtained are analysed for each ovocyte by non-linear regression and a $pIC_{50}$ value was calculated. $pIC_{50}$ designates the negative logarithm of the compound concentration tested needed to reduce the amplitude of the NMDA current by half.

Results: table 1 below gives the $pIC_{50}$ values for certain compounds of the invention. It emerges that, under the test conditions compounds (1a1), (1b), (1c), (1d) and (1e) block the NMDA current in a concentration-dependant manner and are more powerful than ketamine, the NMDA antagonist used clinically.

Given the low bioavailability of ketamine by oral route, we chose the intraperitoneal (ip) route as the sole administration route for in vivo experiments. The analgesic activity of compounds of formula (1) and of ketamine, chosen as the reference compound, were determined in a classical acute inflammatory pain model, intradermal injection of formaldehyde (Bardin et al., 2001, *Eur. J. Pharmacol.*, 421, 109-114).

Protocol: Male rats (Sprague-Dawley Iffa Credo, France) were placed in Plexiglas observation boxes above an angled mirror to facilitate observation of their hind paws. After 30 minutes of acclimatisation, the animals received a formaldehyde injection diluted to 2.5% on the plantar surface of the right hind paw. Injection of formaldehyde produces behavioural responses which occur in two phases:

an early phase, 0 to 5 minutes after injection of formaldehyde, corresponding to stimulation of the receptors specialised in the transmission of nociceptive stimuli;

a late phase which occurs 20 to 30 minutes after injection. This phase corresponds to stimulation of the receptors by inflammatory mediators and/or to hyperexcitation of the dorsal horn induced during the first phase. This later phase therefore brings into play central sensitisation of the pain neurotransmission system in which the glutamate/NMDA system plays a major role. As a result of this, the pain in the second phase is more representative of neuropathic pain than the pain which occurs during the first phase. For this reason, only results obtained in this later phase are taken into consideration in this application.

We selected licking of the paw which received the injection as a behavioural parameter for quantification of pain and chose as the observation periods those periods corresponding to the later phase (in other words, 22.5-27.5 min post-formaldehyde injection). During this 5 min phase, animals are observed every 30 seconds in order to note whether or not the animal is licking the "injected" paw; thus the maximum score is 10. The products of the invention or the carrier are administered by ip route 15 min prior to the injection of formaldehyde.

Results: In this test, the compounds of formula (1a1) and (1e), representative of compounds of the invention, have remarkable analgesic effect (table 2). Thus the minimum significant dose (MSD, the dose needed to significantly reduce licking of the injected paw) for the compounds of formula (1a1) and (1e) is less than that for ketamine. Another advantage of the compounds of formula (1a1) and (1e) compared to ketamine relates to the amplitude of the analgesic effect. In fact we note that at a dose of 40 mg/kg, paw licking is completely inhibited with compounds (1a1) and (1e) whereas it only reaches a 74% reduction with ketamine. Compounds (1a1) and (1e) are therefore more powerful and more effective than ketamine.

TABLE 1

| Compound | Inhibition of NMDA current $pIC_{50}$ |
|---|---|
| 1a1 | 6.3 |
| 1b | 6.3 |
| 1c | 6.8 |
| 1d | 6.4 |
| 1e | 7.1 |
| ketamine | 6.1 |

TABLE 2

| | Paw licking | |
|---|---|---|
| Compound | MSD (mg/kg) | % reduction at 40 mg/kg |
| 1a1 | 10 | 100 |
| 1e | 10 | 100 |
| ketamine | 40 | 75 |

To summarise, the analgesic effect of compounds (1a1) and (1e), representative of compounds of formula (1), is higher than that produced by ketamine in the acute inflammatory pain model in the rat.

We also show that the compounds of the invention have an antidepressant activity in vivo. The antidepressant activities of compounds of formula (1) and of ketamine were determined in a forced swimming model in the rat, a model that is widely used as it is predictive of antidepressant activity in humans.

Protocol: Male rats (Sprague-Dawley Iffa Credo, France) were placed in a cylinder (height 45 cm and diameter 20 cm) filled with water at 25° C.±0.5° C. up to a height of 17 cm. This height allows the rats to swim or to float without their paws touching the base of the cylinder. 24 hours before the test day, the rats are placed in the cylinder for 15 min, after which time they no longer attempt to escape and remain immobile at the surface. On the test day, the compound to be tested or the carrier is injected (ip) into the animal which is placed in the cylinder 30 min later. The duration of immobility (defined when the rat simply floats and only makes small movements to stay at the surface) is measured with an accuracy of 0.1 s for 5 minutes.

Results: In the forced swimming test, the compounds of formulas (1c) and 1(e), representative of the series, significantly reduce the animal's immobility time. When the $ED_{50}$ are compared, that is the doses which reduce immobility time by half relative to control animals, we find that these are lower than for ketamine for compounds (1c) and 1(e), see Table 3. Similarly the amplitude of the anti-immobility effect observed at a dose of 20 mg/kg is greater with compounds (1c) and 1(e) than that obtained with ketamine.

TABLE 3

| Compound | Immobility time | |
|---|---|---|
| | $ED_{50}$ (mg/kg) | % reduction at 20 mg/kg |
| 1c | 13 | 83 |
| 1e | 15 | 77 |
| ketamine | 20 | 50 |

To summarise, compounds (1c) and 1(e), representative of compounds of formula (1), are more powerful and more effective than ketamine in a test predicting antidepressant activity.

We have already highlighted the importance of normalising the NMDA receptor function, in other words blocking its excessive activity without interfering, or interfering as little as possible, with its normal physiological functioning. As a marker of the interaction between the products of the invention and the normal functioning of the NMDA receptors, we chose the pre-pulse inhibition test for the jolt reflex (PPI). This test represents a measurement of the organism's capacity to filter non-essential information. Non-competitive and competitive antagonists as well as channel blockers reduce PPI in the rat (Depoortere et al., 1999, *Behav. Pharmacol.*, 10, 51-62), such a reduction being considered to be predictive of the psychotomimetic effects of NMDA antagonists in humans.

Protocol: Male rats (Sprague-Dawley Iffa Credo, Les Oncins, France) were placed in 18.4 cm by 8.8 cm diameter cylinders resting on a base below which a piezoelectric accelerometer is fixed to act as a detector of the jolt reaction. This is enclosed in a box with a loudspeaker attached to the ceiling to deliver sound pulses and pre-pulses, and is acoustically isolated (SR LAB, San Diego Instruments, San Diego, USA). All the events are controlled by means of software. The animals first undergo a 13 minute pre-test to habituate them to the procedure and to eliminate rats which do not respond to a series of minimum reaction criteria. Three types of sound stimuli (white noise) are delivered; 1) a pulse of 118 dB (P, duration 40 msec); 2) a pre-pulse of 78 dB (duration 20 msec) followed by a pulse of 118 dB (pP); and 3) no pre-pulse or pulse (NP). The interval between the beginning of the pre-pulse and the beginning of the pulse is 100 msec, with background noise at 70 dB. The jolt reaction is recorded for 100 ms, 100 ms after the beginning of the stimulus (pP or NP) by a numerical/analogue acquisition card (12 bits). The session starts with a stimulus-free period of 5 min after which animals are exposed to 10 P (separated on average by 15 s and intended to stabilise the jolt reaction). The reactions recorded with these 10 P are not used for the calculation. After this, 10 P, 10 pP and 3 NP are delivered in a semi-random order with an average interval of 15 s in between. At the end of this pre-test, rats undergo an ip injection of the compounds to be tested or physiological serum as a control and are returned to their cages. The actual test session (similar on every point to the pre-test) is carried out 60 minutes later. The percentage inhibition of the pre-pulse is calculated using data from this test session according to the formula:

(median amplitude $P$−median amplitude $pP$)×100/
(median amplitude $P$).

Results: According to FIG. 1 in the appendix, it appears that compound (1a1) does not disrupt inhibition of the jolt reflex induced by the pre-pulse (PPI) except from a dose of 20 mg/kg. Nevertheless, surprisingly the reduction in PPI is much less pronounced than that observed with ketamine. In fact at a dose of 20 mg/kg ip, ketamine leads to the total disappearance of PPI whereas compound (1a1) only causes a 30% reduction. The PPI reduction nonetheless remains modest even at a dose of 40 mg/kg. Consequently compound (1a1) has a clearly less pronounced tendency than ketamine to cause side effects of central origins.

In summary, the compounds of the invention possess analgesic and antidepressant activity that is superior to that of ketamine in the animal model described above. Surprisingly the compounds of the invention only cause very moderate central effects. It therefore emerges from these experiments that the risk/benefit ratio of the compounds of the invention is clearly more favourable than that of ketamine. As a result of this, the compounds of the present invention as well as pharmaceutical compositions containing a compound of general formula (1) as the active principle or one of its pharmaceutically acceptable salts are potentially useful as medications, particularly in the treatment of certain diseases such as, for example, depression and pain, especially acute or chronic pain, areas in which therapeutic needs are not fully met and for which the discovery of new treatments is therefore highly desirable.

The invention claimed is:
1. Compound of the following general formula (1):

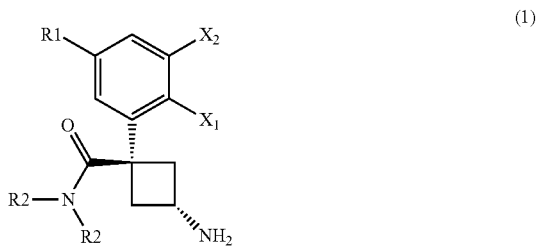

or pharmaceutically acceptable salt or solvate thereof, wherein:
  $X_1$ represents a hydrogen atom or fluorine atom;
  $X_2$ is a hydrogen atom or fluorine atom or chlorine atom;
  R1 represents a hydrogen atom or fluorine atom or chlorine atom or methyl group or methoxy group or cyano group; and
  R2 represents independently or together a methyl group or ethyl group.

2. Compound according to claim 1, wherein:
  $X_1$ represents a hydrogen atom or fluorine atom;
  $X_2$ is a hydrogen atom or fluorine atom or chlorine atom;
  R1 a hydrogen atom or fluorine atom or chlorine atom or methyl group or methoxy group or cyano group;
  R2 is an ethyl group.

3. Compound according to claim 1, chosen from among the following compounds:
  trans-3-amino-N,N-diethyl-1-phenylcyclobutanecarboxamide,
  trans-3-amino-N,N-dimethyl-1-phenylcyclobutanecarboxamide
  trans-3-amino-N,N-diethyl-1-(2-fluorophenyl)-cyclobutanecarboxamide,
  trans-3-amino-N,N-diethyl-1-(3-methoxyphenyl)-cyclobutanecarboxamide,
  trans-3-amino-N,N-diethyl-1-(3-fluorophenyl)-cyclobutanecarboxamide,
  trans-3-amino-N,N-diethyl-1-(3-chlorophenyl)-cyclobutanecarboxamide,
  trans-3-amino-N,N-diethyl-1-(3-methylphenyl)-cyclobutanecarboxamide,
  trans-3-amino-N,N-diethyl-1-(3-cyanophenyl)-cyclobutanecarboxamide,
  trans-3-amino-N,N-diethyl-1-(2-fluoro-3-chlorophenyl)-cyclobutanecarboxamide,
  trans-3-amino-N,N-diethyl-1-(2,5-difluorophenyl)-cyclobutanecarboxamide,
  trans-3-amino-N,N-diethyl-1-(3,5-difluorophenyl)-cyclobutanecarboxamide, and
  trans-3-amino-N,N-diethyl-1-(3,5-dichlorophenyl)-cyclobutanecarboxamide.

4. A method for the treatment of depression which comprises administering to a patient in need thereof an effective amount of a compound according to claim 1.

5. A method for the treatment of pain due to excessive nociception, or neuropathic pain which comprises administering to a patient in need thereof an effective amount of a compound according to claim 1.

6. Pharmaceutical composition comprising at least one compound of general formula (1) according to claim 1, and at least once pharmaceutically acceptable excipient.

7. A method for the treatment of depression which comprises administering to a patient in need thereof an effective amount of a pharmaceutical composition according to claim 6.

8. A method for the treatment of pain due to excessive nociception, or neuropathic pain which comprises administering to a patient in need thereof an effective amount of a pharmaceutical composition according to claim 6.

9. Pharmaceutical composition according to claim 6, which is formulated for oral administration.

10. Pharmaceutical composition according to claim 6, which is formulated for topical administration.

11. Pharmaceutical composition according to claim 6, in the form of a daily dosage unit of a compound of general formula (1) between 1 and 1000 mg.

12. Method for the preparation of compounds of general formula (1) as defined in claim 1, wherein a secondary amine of formula $(R2)_2NH$ is reacted with a compound of formula (C)

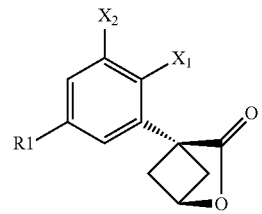

(C)

to give the compound of formula (D)

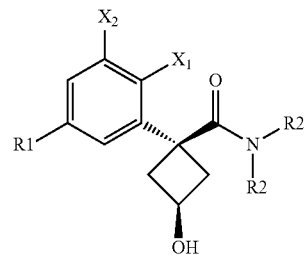

(D)

and the compound of formula (D) is then converted into an amine of formula (1), wherein R1, R2, $X_1$ and $X_2$ are as defined in claim 1.

13. Synthesis intermediates of formula (D)

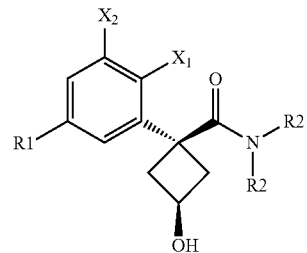

(D)

wherein
  $X_1$ represents a hydrogen atom or fluorine atom;
  $X_2$ is a hydrogen atom or fluorine atom or chlorine atom;
  R1 represents a hydrogen atom or fluorine atom or chlorine atom or methyl group or methoxy group or cyano group; and
  R2 represents independently or together a methyl group or ethyl group.

14. Synthesis intermediates of formula (C)

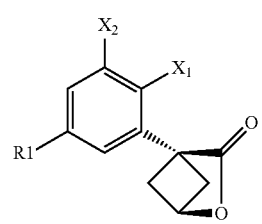

(C)

wherein
- $X_1$ represents a hydrogen atom or fluorine atom;
- $X_2$ is a hydrogen atom or fluorine atom or chlorine atom; and
- R1 represents a hydrogen atom or fluorine atom or chlorine atom or methyl group or methoxy group or cyano group.

* * * * *